(12) United States Patent
Dastjerdi et al.

(10) Patent No.: US 11,617,614 B2
(45) Date of Patent: *Apr. 4, 2023

(54) MULTI-PROBE SYSTEM USING BIPOLAR PROBES AND METHODS OF USING THE SAME

(71) Applicant: MEDTRONIC HOLDING COMPANY SÀRL, Tolochenaz (CH)

(72) Inventors: Ahmad Khayer Dastjerdi, Toronto (CA); Robert Harrison, Milton (CA); Neil Godara, Milton (CA); Michael Same, Toronto (CA); Kathryn Atwell, Etobicoke (CA); Travis Nolan, Collierville, TN (US)

(73) Assignee: MEDTRONIC HOLDING COMPANY SÀRL, Tolochenaz (CH)

( * ) Notice: Subject to any disclaimer, the term of this patent is extended or adjusted under 35 U.S.C. 154(b) by 288 days.

This patent is subject to a terminal disclaimer.

(21) Appl. No.: 17/121,978

(22) Filed: Dec. 15, 2020

(65) Prior Publication Data
US 2021/0093373 A1    Apr. 1, 2021

Related U.S. Application Data

(63) Continuation of application No. 15/387,291, filed on Dec. 21, 2016, now Pat. No. 10,864,040, which is a
(Continued)

(51) Int. Cl.
*A61B 18/14*    (2006.01)
*A61B 18/00*    (2006.01)

(52) U.S. Cl.
CPC .............. *A61B 18/1482* (2013.01); *A61B 2018/00023* (2013.01); *A61B 2018/00339* (2013.01);
(Continued)

(58) Field of Classification Search
CPC ...... A61B 18/1482; A61B 2018/00023; A61B 2018/00339; A61B 2018/00577; A61B 2018/00791

See application file for complete search history.

(56) References Cited

U.S. PATENT DOCUMENTS 5,370,675 A    12/1994    Edwards et al.
5,383,874 A    1/1995    Jackson et al.
(Continued)

FOREIGN PATENT DOCUMENTS

AU    2012200903    1/2013
CN    100460031    2/2009
(Continued)

*Primary Examiner* — Tigist S Demie

(57) ABSTRACT

A multi-probe system and a method of lesioning for targeting a region of a vertebral body are disclosed. The method includes inserting a first introducer assembly into a first target location of the vertebral body to provide a first trajectory to access the vertebral body, the first introducer assembly including a first cannula. The method also includes inserting a second introducer assembly into a second target location of the vertebral body to provide a second trajectory to access the vertebral body, the second introducer assembly including a second cannula. The method further includes inserting a first bipolar probe through the first cannula of the first introducer assembly, the first bipolar probe including a first active tip at a distal end of the first bipolar probe, the first active tip including at least two electrodes. The method includes inserting a second bipolar probe through the second cannula of the second introducer assembly, the second bipolar probe including a second active tip at a distal end of the second bipolar probe, the second active tip including at least two electrodes.

15 Claims, 30 Drawing Sheets

Related U.S. Application Data continuation of application No. 62/272,379, filed on Dec. 29, 2015.

(52) U.S. Cl.
CPC .............. *A61B 2018/00577* (2013.01); *A61B 2018/00791* (2013.01)

(56) References Cited

U.S. PATENT DOCUMENTS

| | | |
|---|---|---|
| 5,391,199 A | 2/1995 | Ben-Haim |
| 5,472,441 A | 12/1995 | Edwards et al. |
| 5,505,730 A | 4/1996 | Edwards |
| 5,536,267 A | 7/1996 | Edwards et al. |
| 5,582,609 A | 12/1996 | Swanson et al. |
| 6,332,089 B1 | 12/2001 | Acker et al. |
| 6,575,969 B1 | 6/2003 | Rittman, III et al. |
| 6,690,963 B2 | 2/2004 | Ben-Haim et al. |
| 7,167,748 B2 | 1/2007 | Ben-Haim et al. |
| 7,238,182 B2 | 7/2007 | Swoyer et al. |
| 7,257,450 B2 | 8/2007 | Auth et al. |
| 7,266,414 B2 | 9/2007 | Cornelius et al. |
| 7,318,823 B2 | 1/2008 | Sharps et al. |
| 7,335,196 B2 | 2/2008 | Swanson et al. |
| 7,354,436 B2 | 4/2008 | Rioux et al. |
| 7,367,974 B2 | 5/2008 | Haemmerich et al. |
| 7,445,618 B2 | 11/2008 | Eggers et al. |
| 7,507,236 B2 | 3/2009 | Eggers et al. |
| 7,530,980 B2 | 5/2009 | Hooven |
| 7,601,149 B2 | 10/2009 | DiCarlo et al. |
| 7,678,108 B2 | 3/2010 | Christian et al. |
| 7,776,035 B2 | 8/2010 | Rick et al. |
| 7,819,863 B2 | 10/2010 | Eggers et al. |
| 8,182,477 B2 | 5/2012 | Orzulak et al. |
| 8,361,067 B2 | 1/2013 | Pellegrino et al. |
| 8,663,216 B2 | 3/2014 | Davison et al. |
| 8,734,439 B2 | 5/2014 | Gough et al. |
| 9,008,793 B1 | 4/2015 | Cosman, Sr. et al. |
| 9,044,245 B2 | 6/2015 | Condie et al. |
| 9,289,618 B1 | 3/2016 | Ben-Haim et al. |
| 9,345,537 B2 | 5/2016 | Harrison et al. |
| 9,474,573 B2 | 10/2016 | Leung et al. |
| 9,539,052 B2 | 1/2017 | Edwards et al. |
| 9,598,691 B2 | 3/2017 | Davalos |
| 9,610,110 B2 | 4/2017 | Truckai et al. |
| 2005/0177210 A1* | 8/2005 | Leung .................. A61B 18/148 607/101 |
| 2005/0209659 A1* | 9/2005 | Pellegrino .......... A61B 18/1477 607/99 |
| 2006/0200121 A1 | 9/2006 | Mowery |
| 2007/0027449 A1 | 2/2007 | Godara |
| 2007/0112348 A1 | 5/2007 | Eggers et al. |
| 2007/0179497 A1 | 8/2007 | Eggers et al. |
| 2008/0021447 A1 | 1/2008 | Davison et al. |
| 2008/0281312 A1 | 11/2008 | Werneth et al. |
| 2009/0005774 A1 | 1/2009 | Fernald |
| 2009/0069807 A1 | 3/2009 | Eggers et al. |
| 2009/0171340 A1 | 7/2009 | Young |
| 2009/0269317 A1 | 10/2009 | Davalos |
| 2009/0287202 A1 | 11/2009 | Ingle et al. |
| 2010/0130976 A1 | 5/2010 | Bystryak et al. |
| 2010/0152725 A1 | 6/2010 | Pearson et al. |
| 2010/0168725 A1 | 7/2010 | Babkin et al. |
| 2011/0230874 A1 | 9/2011 | Epstein et al. |
| 2011/0238057 A1 | 9/2011 | Moss et al. |
| 2011/0288543 A1 | 11/2011 | Cheng et al. |
| 2012/0046656 A1 | 2/2012 | Brannan |
| 2012/0095459 A1 | 4/2012 | Callas et al. |
| 2012/0172872 A1 | 7/2012 | Nollert et al. |
| 2012/0310230 A1 | 12/2012 | Willis |
| 2013/0096549 A1 | 4/2013 | Organ et al. |
| 2014/0022245 A1 | 1/2014 | Brannan et al. |
| 2014/0025066 A1 | 1/2014 | Kerr |
| 2014/0257265 A1 | 9/2014 | Godara et al. |
| 2014/0276702 A1 | 9/2014 | McKay et al. |
| 2015/0238251 A1 | 8/2015 | Shikhman et al. |
| 2016/0058493 A1 | 3/2016 | Robert et al. |
| 2016/0058492 A1 | 5/2016 | Yates et al. |
| 2016/0235471 A1 | 8/2016 | Godara et al. |
| 2016/0270841 A1 | 9/2016 | Strobl et al. |
| 2016/0270845 A1 | 9/2016 | Benscoter et al. |
| 2017/0000553 A1 | 1/2017 | Weiner et al. |
| 2017/0049503 A1 | 2/2017 | Cosman |
| 2017/0049513 A1 | 2/2017 | Cosman et al. |

FOREIGN PATENT DOCUMENTS

| | | |
|---|---|---|
| EP | 1493397 | 9/2011 |
| EP | 2874707 | 5/2015 |
| EP | 3030185 | 6/2016 |
| EP | 3137006 | 3/2017 |
| GB | 2453601 | 7/2010 |
| WO | 2008142686 | 11/2008 |
| WO | 2010009150 | 1/2010 |
| WO | 2016127162 | 8/2011 |
| WO | 2015200518 | 12/2015 |
| WO | 2016123608 | 8/2016 |
| WO | 2016126778 | 8/2016 |
| WO | 2016148954 | 9/2016 |
| WO | 2017031362 | 2/2017 |

* cited by examiner

MULTI-PROBE SYSTEM USING BIPOLAR PROBES AND METHODS OF USING THE SAME

RELATED APPLICATIONS

The present application is a continuation of U.S. application Ser. No. 15/387,291, filed Dec. 21, 2016; and claims benefit of U.S. Provisional Application No. 62/272,379, filed Dec. 29, 2015; all of which are incorporated by reference herein.

BACKGROUND

The present invention relates to bipolar devices for use in the treatment of bone tissue. More specifically, the present invention relates to a multi-probe bipolar radio-frequency (RF) ablation system for bone tumor ablation.

Embodiments of the present invention provide a multi-probe bipolar lesioning system for treating bone tissue that overcomes disadvantages of conventional ablation systems. Current RF ablation systems for bone tumor ablation are limited in the volume of tissue that they can ablate. Some systems use articulating features, while others use individual RF probes with varying active tip dimensions. None of the existing systems may be able to ablate reliably the medial and posterior-medial aspects of the vertebral body due to the nature of the surgical access. The variation of tumor location within a vertebral body poses a challenge, as the access to the vertebral body is typically limited to transpedicular approaches. As such, there is a need for a system that would provide a comprehensive solution to this problem, where the system provides targeting of the medial and posteromedial aspects using standard techniques.

SUMMARY

The present invention contemplates a method of lesioning for targeting a region of a vertebral body. The method includes inserting a first introducer assembly into a first target location of the vertebral body to provide a first trajectory to access the vertebral body, the first introducer assembly including a first cannula. The method also includes inserting a second introducer assembly into a second target location of the vertebral body to provide a second trajectory to access the vertebral body, the second introducer assembly including a second cannula. The method further includes inserting a first bipolar probe through the first cannula of the first introducer assembly, the first bipolar probe including a first active tip at a distal end of the first bipolar probe, the first active tip including at least two electrodes. The method additionally includes inserting a second bipolar probe through the second cannula of the second introducer assembly, the second bipolar probe including a second active tip at a distal end of the second bipolar probe, the second active tip including at least two electrodes. The method includes positioning the first active tip of the first bipolar probe within the vertebral body. The method also includes positioning the second active tip of the second bipolar probe within the vertebral body. The method further includes supplying power to the first bipolar probe to create a first lesion around the first active tip, and the method additionally includes supplying power to the second bipolar probe to create a second lesion around the second active tip, the supplying power to the first bipolar probe being independent from the supplying power to the second bipolar probe.

The present invention further contemplates the method including the inserting of the first introducer assembly being inserted through a first pedicle, the inserting of the second introducer assembly being inserted through a second pedicle; and the first pedicle being angled within a range of approximately 15-25 degrees oblique to a mid-sagittal plane, the second pedicle being angled within a range of approximately 15-25 degrees oblique to the mid-sagittal plane, the first pedicle and the second pedicle being on different sides of the mid-sagittal plane.

The present invention also contemplates the method including determining an ablation zone to be targeted within the vertebral body; and determining a size of the first lesion and the second lesion that would cover the ablation zone.

The present invention additionally contemplates the method including cooling, internally, the first bipolar probe and the second bipolar probe during the supplying power to the first bipolar probe and the supplying power to the second bipolar probe.

The present invention moreover contemplates the method including the inserting of the first introducer assembly and the inserting of the second introducer assembly using a transpedicular approach.

The present invention further contemplates the method including the inserting of the first introducer assembly and the inserting of the second introducer assembly using a bi-lateral approach.

The present invention also contemplates the method including the inserting of the first introducer assembly and the inserting of the second introducer assembly using an extrapedicular approach.

The present invention additionally contemplates the method including the positioning the first active tip and the positioning the second active tip creating an angle between the first active tip and the second active tip; and the angle between the first active tip and the second active tip being approximately 40 degrees to facilitate access to an anterior region of the vertebral body.

The present invention moreover contemplates the method including the angle between the first active tip and the second active tip being approximately 110 degrees to facilitate access to a posterior region of the vertebral body.

The present invention further contemplates the method including the supplying power to the first bipolar probe and the supplying power to the second bipolar probe occurring simultaneously.

The present invention also contemplates the method including the supplying power to the first bipolar probe and the supplying power to the second bipolar probe occurring at different times.

The present invention additionally contemplates the method including the supplying power to the first bipolar probe and the supplying power to the second bipolar probe causing a symbiotic lesion growth between the first bipolar probe and the second bipolar probe; and the symbiotic lesion growth creating a resultant lesion that is greater than the first lesion and the second lesion combined.

The present invention moreover contemplates the method including the supplying power to the first bipolar probe and the supplying power to the second bipolar probe allowing for a negative co-operation lesion between the first bipolar probe and the second bipolar probe; and the negative co-operation lesion being less than the first lesion and the second lesion combined.

The present invention further contemplates the method including measuring temperature of an area surrounding the first active tip of the first bipolar probe; measuring temperature of an area surrounding the second active tip of the second bipolar probe; and adjusting the supplying power to the first bipolar probe based on the measuring temperature of the area surrounding the first active tip of the first bipolar probe.

The present invention also contemplates the method including adjusting the supplying power to the second bipolar probe based on the measuring temperature of the area surrounding the second active tip of the second bipolar probe; and identifying ablation parameters and relative placement of the first bipolar probe and the second bipolar probe to achieve a desired ablation volume for the positioning the first active tip and the positioning the second active tip.

In one broad aspect, embodiments of the present invention comprise a multi-probe bipolar lesioning system that allows two or more bipolar probes to be used simultaneously in order to treat bone tissue.

As a feature of this broad aspect, the system allows for ablating a wide variety of bone tissue volumes using standard surgical access.

As a feature of this broad aspect, the multi-probe bipolar system is usable to treat a vertebral body. In one such example, the multi-probe bipolar system allows for two bi-polar probes to be positioned bilaterally (on both sides of the vertebral body) within the vertebral body using a transpedicular approach to allow for substantially simultaneous lesioning within the vertebral body. In one such example, the multi-probe bipolar system is usable to treat a vertebral body having a tumor therein.

In a further broad aspect, embodiments of the present invention comprise a multi-probe bipolar system comprising two bipolar probes that provides temperature controlled power delivery to allow energy to be delivered to each of the two bipolar probes independently.

As a feature of this aspect, the two bipolar probes are positioned relative to each other to allow for separate lesions to be created independently around each probe.

As another feature of this aspect, the two bipolar probes are positioned relative to each other to allow for two lesions to be created independently around each probe, and additionally enables positive co-operation between the two probes that allows for co-operative or symbiotic lesion growth between the two probes, where the resultant lesion is greater than the two independent lesions that would otherwise be formed around each probe.

As another feature of this aspect, the two bipolar probes may be positioned relative to each other to allow for negative co-operation between the two probes where the resultant lesion is less than two independent lesions that would otherwise be formed around each probe.

These and other objects of the present invention will be apparent from a review of the following specification and the accompanying drawings.

BRIEF DESCRIPTION OF THE DRAWINGS

In order that the invention may be readily understood, embodiments of the invention are illustrated by way of examples in the accompanying drawings, in which.

DETAILED DESCRIPTION

Figure 1:
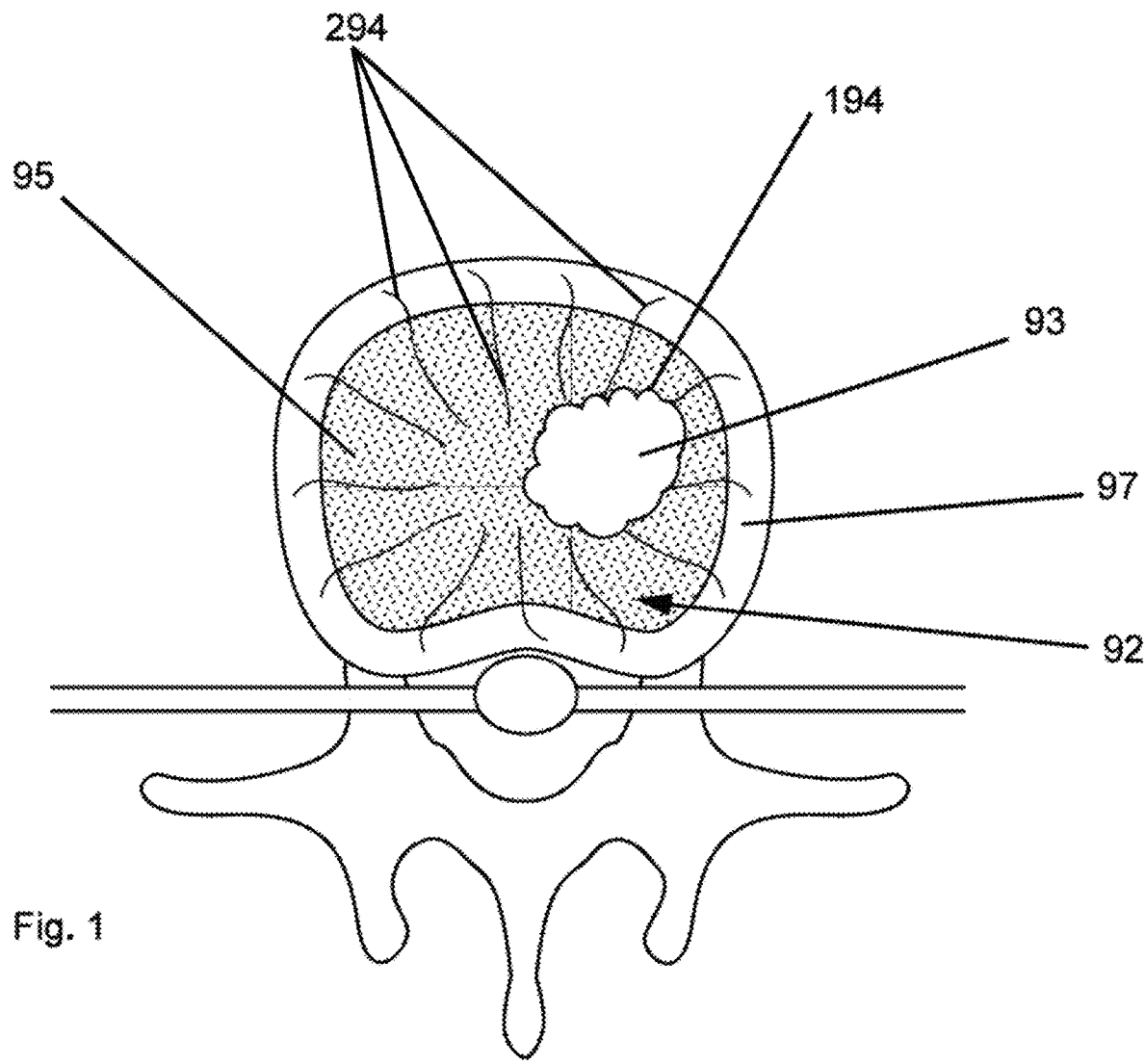
FIG. 1 illustrates a top schematic view of a target location in a vertebral bone.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 2A:
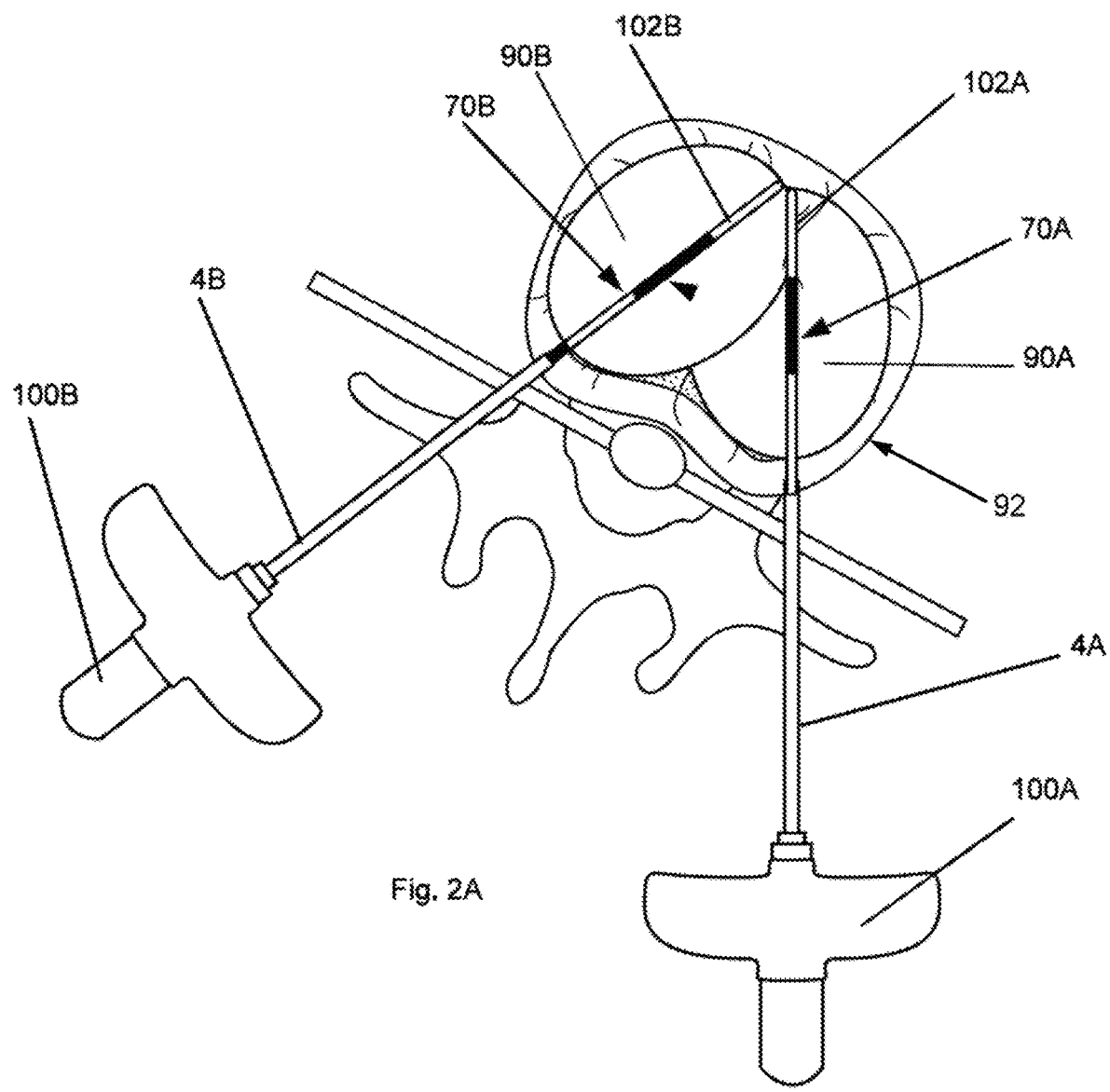
FIG. 2A illustrates a top schematic view of the target location and the positioning of a first bipolar probe and a second bipolar probe in a vertebral body.
Figure 2B:
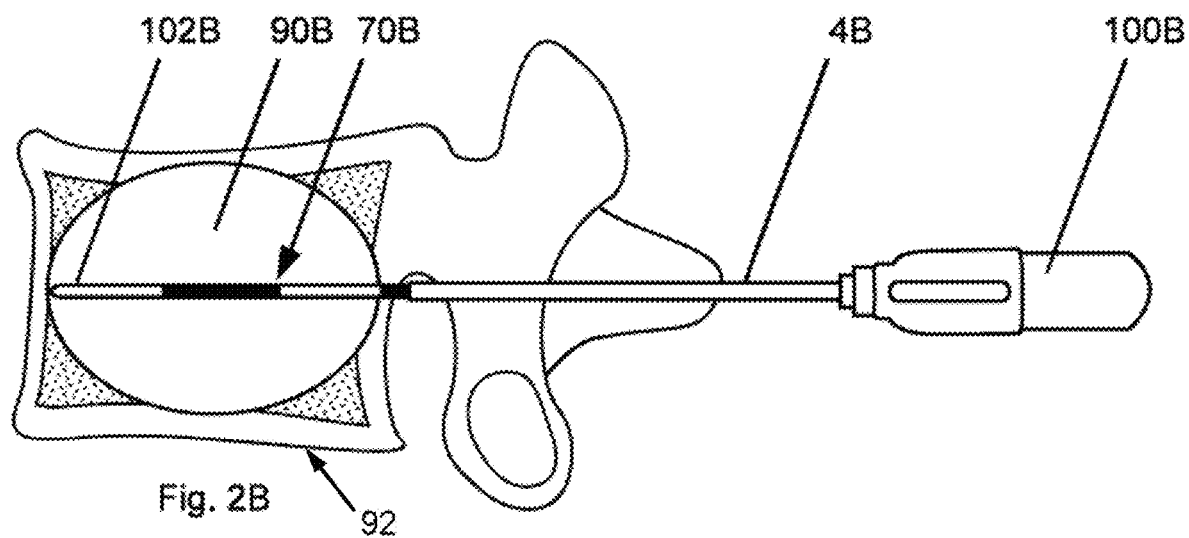
FIG. 2B illustrates a side schematic view of the target location and one of the first and second bipolar probes positioned with respect thereto.

A system of the present invention was designed to ablate a wide variety of bone tissue volumes using standard surgical access. More specifically, the present inventors have discovered a multi-probe bipolar lesioning system that allows two or more bipolar probes to be used simultaneously in order to treat bone tissue, such as within a vertebral body. For example, a medial and a posteromedial region of the vertebral body can be targeted using the multi-probe bipolar lesioning system. In some embodiments, the two probes are not delivering energy at the same instance of time. In some such embodiments, the multi-probe bipolar lesioning system comprises two bipolar probes 100A, 100B. In some embodiments, the two bipolar probes 100A, 100B may be cooled RF bipolar probes 100A, 100B that each comprising coaxial bipolar ablation electrodes that are internally cooled. The cooled RF bipolar probes 100A, 100B are usable simultaneously or individually to treat a vertebral body 92 (shown in FIG. 1). The two bipolar probes 100A, 100B may be placed within the vertebral body 92 as shown in FIGS. 2A and 2B. The bipolar probes 100A, 100B may be positioned adjacent a tumor 93 within the vertebral body 92 at a bone-tumor interface 194, and may be usable to destroy nervous tissue generating pain signals at the bone-tumor interface 194.

In some embodiments, the cooled RF bipolar probes 100A, 100B may be advanced into the vertebral body 92 until a distal end 102A, 102B of each of the bipolar probes 100A, 100B is positioned at the bone-tumor interface 194 at the edge of the tumor 93 adjacent to nerves 294. In one example, probe active tips 70A, 70B for each of the bipolar probes 100A, 100B, respectively, may be positioned within a trabecular bone 95 within the vertebral body 92 that is encased by an electrically insulative cortical bone 97. In some embodiments, the two or more bipolar probes 100A, 100B may be positioned substantially adjacent the rich nerve supply within the vertebral body 92. In other embodiments, the bipolar probes 100A, 100B may be positioned within or substantially adjacent to the vertebral body 92 in proximity to sensitive structures such as the cortical bone 97 that may be non-conductive, or in other words, may have a low electrical conductivity.

In some embodiments, as mentioned above, the target location is the vertebral body 92 and the multi-probe bipolar system is used to treat the vertebral body 92, as shown in FIGS. 2A and 2B. In some such embodiments, an introducer assemblies 4A, 4B may be used to facilitate placement of the bipolar probes 100A, 100B, respectively, of the multi-probe bipolar system. The introducer assemblies 4A, 4B may comprise a cannula with a stylet disposed therein, and may be inserted and advanced to the target location within a patient's body.

In a particular embodiment of a method of the present invention, a bi-pedicular approach is used where the multi-probe cooled RF bipolar system comprises the two bipolar probes 100A, 100B, where each of the bipolar probes 100A, 100B is advanced into the vertebral body 92 using a trans-pedicular approach.

In one such embodiment, the first introducer assembly 4A is inserted into the vertebral body 92 using the transpedicular approach. More specifically, the first introducer assembly 4A is inserted through the first pedicle (the right pedicle), in order to provide a trajectory to access the vertebral body 92. The first bipolar probe 100A may then be inserted through the cannula and advanced to the target site within the vertebral body 92. The second introducer assembly 4B is inserted into the vertebral body 92, also using a transpedicular approach. The second introducer assembly 4B is inserted through the second pedicle (the left pedicle) and also provides a trajectory to access the vertebral body 92. The second bipolar probe 100B may then be inserted through the cannula and advanced to the target site within the vertebral body 92.

In some such embodiments, the two bipolar probes 100A, 100B are inserted and positioned within the vertebral body 92 using a bi-lateral approach to allow for substantially simultaneous lesioning using the two bipolar probes 100A, 100B. In some such embodiments, energy may be delivered through only one of the two bipolar probes 100A, 100B at a given moment of time.

Figure 3:
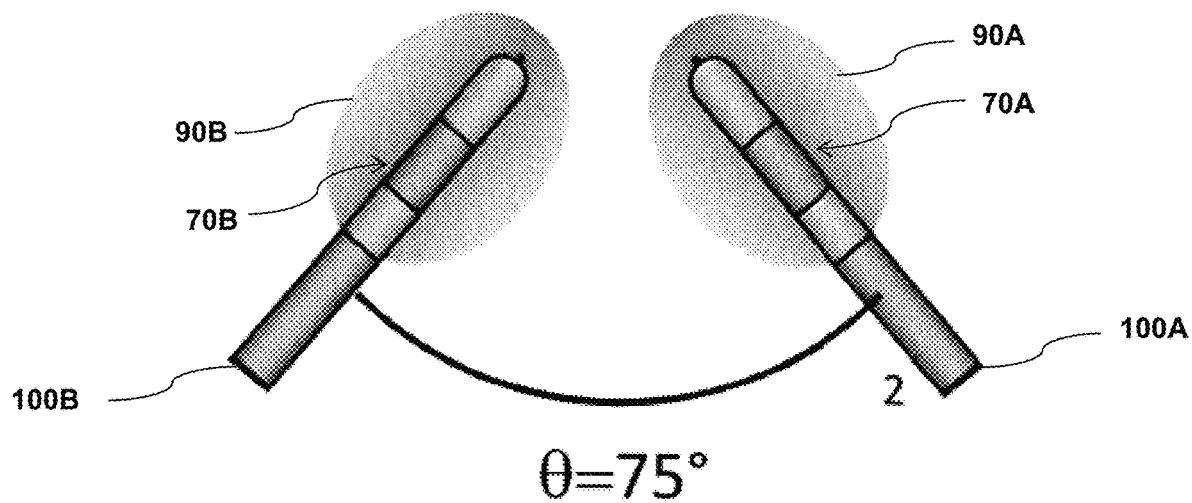
FIG. 3 illustrates a top schematic view of the positioning of the ends of the first and second bipolar probes.
Figure 4:
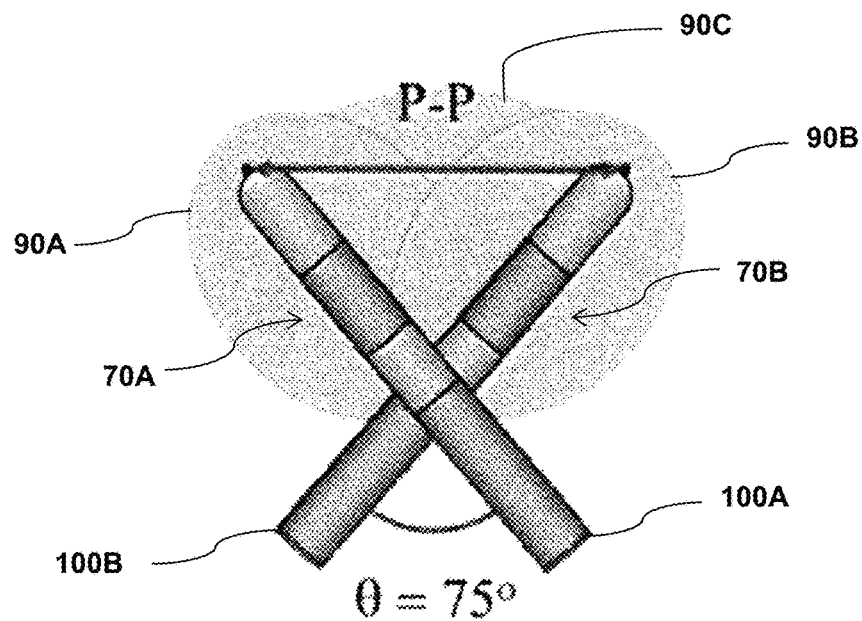
FIG. 4 illustrates another top schematic view of the positioning of the ends of the first and second bipolar probes.

In other embodiments, the introducer assemblies 4A, 4B may be inserted through the pedicle at any another suitable angle. Alternatively, in some embodiments, the introducer assemblies 4A, 4B may be inserted through a variety of angles in the sagittal/coronal planes. In some such embodiments, the bipolar probes 100A, 100B may be inserted with a relative angle of 75° with respect to one another, as shown in FIGS. 3 and 4. The angle of 75° may represent the nominal angle between the pedicles of a typical vertebra. In still other examples, the two bipolar probes 100A, 100B may be positioned within the vertebral body 92 using an extra-pedicular approach. In some such examples, the distance between the probe active tips 70A, 70B may be varied to provide various lesion sizes. In some embodiments, the angle between the bipolar probes 100A, 100B may be about 40° to facilitate access to the back or anterior region of the vertebral body 92 to permit lesioning therein. In another embodiment, the angle between the two bipolar probes 100A, 100B may be about 110° to allow for access to the posterior region of the vertebral body 92. In some examples, the bipolar probes 100A, 100B may be inserted along a symmetric plane of the vertebral body 92.

In one particular example, the introducer assemblies 4A, 4B may be inserted through the pedicle at an angle of about 15° to about 25° oblique to the mid-sagittal plane, which provides a trajectory to access the vertebral body 92. The first bipolar probe 100A may then be inserted through the cannula of the first introducer assembly 4A and advanced to the target site. As such, the first bipolar probe 100A is inserted into the vertebral body 92 at a first target location to the right of the mid-sagittal plane at an angle of about 15° to about 25° to the mid-sagittal plane. The second introducer assembly 4B may be inserted through the second pedicle at an angle of about 15° to about 25° oblique to the mid-sagittal plane, which also provides a trajectory to access the vertebral body 92. The second bipolar probe 100B may then be inserted through the cannula of the second introducer assembly 4B and advanced to the target site. As such, the second bipolar probe 100B is inserted into the vertebral body 92 at a second target location to the left of the mid-sagittal plane at an angle of about 15° to about 25° from the mid-sagittal plane.

In accordance with a method of the present invention, energy may be supplied to the first and second bipolar probes 100A, 100B to allow for a first bipolar lesion 90A to be formed at a first location within the vertebral body 92 using the first bipolar probe 100A, and a second bipolar lesion 90B to be formed at a second location within the vertebral body 92 using the second bipolar probe 100B. In some embodiments, this may allow for the simultaneous use of the first and second bipolar probes 100A, 100B to substantially concurrently create lesions within the vertebral body 92. In one example, these lesions may be referred to as bi-lateral lesions, where the bi-lateral lesions refer to lesions that are simultaneously created on both sides of the vertebral body 92. In some examples, RF electrical energy is delivered primarily on only a given probe at a moment in time. As such, in some embodiments, the system of the present invention allows for "concurrent lesioning" using the two bipolar probes 100A, 100B. In some examples, while the lesions are created at the same time, energy delivery does not occur simultaneously on both bipolar probes 100A, 100B.

Bipolar lesions of different geometry can be created by manipulating the duration and intensity of energy delivered through each of the bipolar probes 100A, 100B in the multi-probe bipolar lesioning system. In some embodiments, an RF generator is provided that supplies RF energy to each of the bipolar probes 100A, 100B in a bipolar manner. In one example, the power output of the RF generator may be temperature controlled. In some such embodiments, direct tissue temperature monitoring is used in conjunction with internal cooling when supplying RF power to form a lesion. The power output may be adjusted based on the measured temperature response of the tissue to RF heating under cooling. The temperature response of the target tissue may be monitored using a temperature sensor such as a thermocouple. In one particular example the thermocouple may be coupled to the distal ends 102A, 102B of the probes 100A, 100B.

In some embodiments of a multi-probe bipolar lesioning system, as discussed above, the two cooled RF bipolar probes 100A, 100B are provided that may be used simultaneously to allow for a lesion to be created around each bipolar probe 100A, 100B. In some such embodiments of the present invention, the multi-probe bipolar ablation system of the present invention may be used for the ablation of the vertebral body 92, including the ablation of metastatic malignant lesions in the vertebral body 92. The system permits the two cooled RF bipolar probes 100A, 100B that each comprise coaxial bipolar ablation electrodes to be used simultaneously. The two bipolar probes 100A, 100B can be matched or mismatched in terms of the ablation volumes they generate. RF electrical energy is delivered on only a given bipolar probe 100A, 100B at a moment in time. However, energy delivery may switch between the two bipolar probes 100A, 100B so rapidly that the tissue around each bipolar probe 100A, 100B can be heated simultaneously. The thermal zone of effect of each bipolar probe 100A, 100B is such that it may cooperate, either positively or negatively, with the ablation zone of the other bipolar probe 100A, 100B. The angle of approach, ablation parameters, and probe sizes can be selected to create a wide variety of lesion forms and geometries. When cooperating positively, the ablation zones can interact in such a way so as to ablate the posterior-medial aspect of the vertebral body 92. More specifically, some embodiments of the present invention provide the two internally cooled bipolar probes 100A, 100B comprising coaxial bipolar RF electrodes, and provide an algorithm for identifying the appropriate bipolar probes 100A, 100B, ablation parameters, and relative placement of the probes so as to achieve a desired ablation volume. In other embodiments, the multi-probe bipolar ablation system may comprise three or more bipolar probes. In some embodiments, the two internally cooled coaxial bipolar probes 100A, 100B form two independent isolated systems. In some such examples, both of the bipolar probes 100A, 100B are capable of creating lesions simultaneously but power is not delivered to both of the bipolar probes 100A, 100B at the same time.

In other embodiments, the relationship between ablation parameters and symbiotic ablation growth may vary.

In one example of a method of the present invention, a method of ablating a region of tissue within the vertebral body 92 is provided comprising the following steps: (1) determining the ablation zone to be targeted within the vertebral body 92 (in some examples, this may be done pre-operatively); (2) determining the size of the lesion that would suitably cover the desired ablation zone. In some examples, this involves determining the long and short axis of the ellipsoid that could cover the ablation zone.

This step (2) may involve additionally determining if a desired ablation zone can be effectively covered by a single RF probe. If this is the case, then the appropriate bipolar probe 100A, 100B is selected (either up-sized or a serial "sausage-link" chain of ablations using a down-sized RF electrode). On the other hand, if it is determined that an ablation zone is of a particular size or situated in such a position that it requires bilateral access (requiring the two RF bipolar probes 100A, 100B inserted through individual left and right pedicles), then the two bipolar probes 100A, 100B are appropriately selected. In some such embodiments, the desired volume of ablation determined by the user is matched to the ablation zone.

Figure 5:
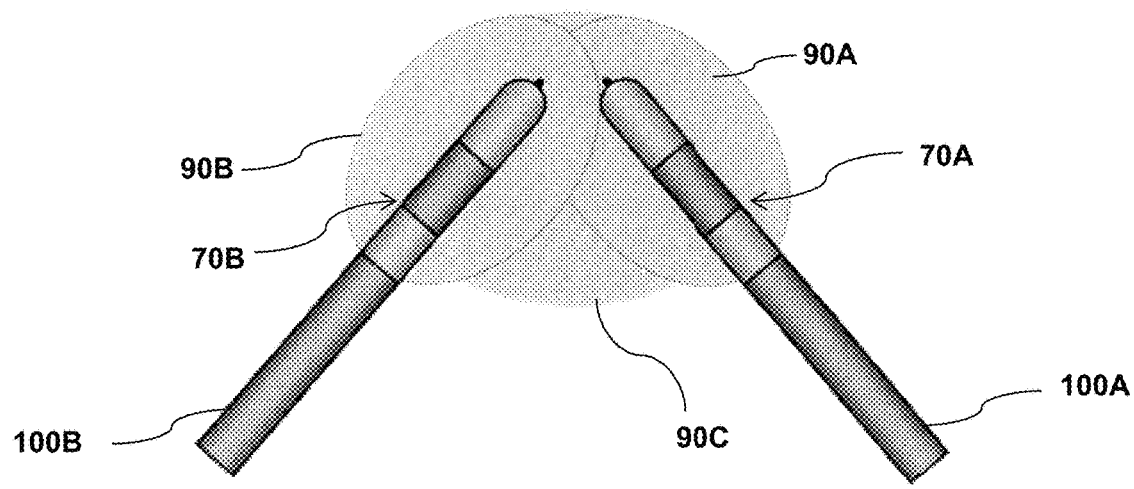
FIG. 5 illustrates still another top schematic view of the positioning of the ends of the first and second bipolar probes.

In some such embodiments, if the desired ablation zone is greater than what would be ablated by the simple addition of the ablation zones created by the two RF bipolar probes 100A, 100B, then the two bipolar probes 100A, 100B can be positioned relative to each other so as to symbiotically create a third zone of ablation 90C between the two bipolar probes 100A, 100B, as shown in FIGS. 4 and 5. In one such example, the third zone of ablation 90C is formed through co-operative lesioning through symbiotic growth due to thermal trapping between the individual ablation zones of the two RF bipolar probes 100A, 100B. In some such examples, each lesion grows independently around each of the two RF bipolar probes 100A, 100B until there is heating between the two ablation zones, thereby forming the third zone of ablation 90C. The resultant lesion is larger than the two individual lesions that would have formed around each of the bipolar probes 100A, 100B in the absence of symbiosis. The third zone of ablation 90C forms as a result of the inability of the tissue between the two bipolar probes 100A, 100B to effectively dissipate the heat from the two bipolar probes 100A, 100B.

In some such examples, the nature of the symbiotic growth is a function of: (i) the combination of the two RF bipolar probes used (gauge, RF electrode length, treatment temperature, treatment time). A graph of the symbiotic growth is provided in FIGS. 6-22. In some embodiments of the present invention, a table may be provided that outlines the features and properties that govern the symbiotic relationship.

Based on the selection as per step (2) above, RF energy may be delivered to the patient.

In some embodiments described above, the two bipolar probes 100A, 100B may be positioned relative to one another to allow for negative co-operation between the two bipolar probes 100A, 100B where the resultant lesion may be less than two independent lesions that would otherwise have formed around each probe 100A, 100B. In some such embodiments, the bipolar probes 100A, 100B may be positioned close to one another such that the thermocouple of one probe (e.g., the bipolar probe 100A) sees a higher temperature due to power delivery from the other probe (e.g., the bipolar probe 100B), which may result in the system not delivering as much power to the first bipolar probe (e.g., the bipolar probe 100A), which may result in a smaller lesion size of the resultant lesion.

In an alternative embodiment of the present invention, alternate energy delivery methods such as ultrasound or microwave may be used that may be capable of accomplishing substantially the same outcome. In still a further alternative, a navigable system (steerable) may be provided. In some such examples, the navigable system may be used alternatively to or in conjunction with embodiments that provide for symbiotic lesion growth. In an additional alternative of the present invention, the physician may attempt to access the vertebral body 92 from different angles so that the area (at least some of the area or substantially the area) that is otherwise ablated using symbiotic growth may be directly placed within the ellipsoid of a "normal" ablation zone.

Some embodiments of the present invention provide a temperature controlled system where the temperature parameter is used towards/to facilitate symbiotic lesion growth. In some examples, the system of the present invention provides for temperature controlled power delivery where the system comprises the two or more cooled-tip RF bipolar probes 100A, 100B with each probe 100A, 100B comprising bipolar electrodes. The system of the present invention, in some embodiments, is usable for ablation of bone tumors. Furthermore, some embodiments of the present invention provide information on the degree of symbiosis between the bipolar probes 100A, 100B (and lesions formed thereby) in a multi-probe bipolar system.

In some examples, the present invention provides for symbiotic growth of lesion between multiple cooled RF electrodes for the purposes of bone ablation. In some examples, embodiments of the present invention provide a multi-probe cooled RF bipolar ablation system that facilitates ablation in bone tissue that may have reduced electrical conductivity. The system provides a means to create a symbiotic relationship during lesion formation and provides a clinical methodology that facilitates ablation accordingly.

In one broad aspect, embodiments of the present invention comprise a multi-probe bipolar lesioning system that allows the two or more bipolar probes 100A, 100B to be used simultaneously in order to treat bone tissue.

As a feature of this broad aspect, the system allows for ablating a wide variety of bone tissue volumes using standard surgical access.

As a feature of this broad aspect, the multi-probe bipolar system is usable to treat the vertebral body 92. In one such example, the multi-probe bipolar system allows for the two bipolar probes 100A, 100B to be positioned bilaterally (on both sides of the vertebral body 92) within the vertebral body 92 using a transpedicular approach to allow for substantially simultaneous lesioning within the vertebral body 92. In one such example, the multi-probe bipolar system is usable to treat the vertebral body 92 having the tumor 93 therein.

In a further broad aspect, embodiments of the present invention comprise a multi-probe bipolar system comprising the two bipolar probes 100A, 100B that provides temperature controlled power delivery to allow energy to be delivered to each of the two bipolar probes 100A, 100B independently.

As a feature of this aspect, the two bipolar probes 100A, 100B are positioned relative to each other to allow for separate lesions to be created independently around each bipolar probe 100A, 100B.

As another feature of this aspect, the two bipolar probes 100A, 100B are positioned relative to each other to allow for two lesions to be created independently around each bipolar probe 100A, 100B, and additionally enables positive co-operation between the two bipolar probes 100A, 100B that allows for co-operative or symbiotic lesion growth between the two bipolar probes 100A, 100B, where the resultant lesion is greater than the two independent lesions that would otherwise be formed around each bipolar probe 100A, 100B.

As another feature of this aspect, the two bipolar probes 100A, 100B are positioned relative to each other to allow for negative co-operation between the two bipolar probes 100A, 100B where the resultant lesion is less than two independent lesions that would otherwise be formed around each bipolar probe 100A, 100B.

Some embodiments of the present invention may utilize an RF Ablation System, including an OsteoCool RF Generator, an OsteoCool Pump, OsteoCool Extension Cable, and an OsteoCool probe having distal ends of 10 mm. RF Procedure Settings may include an RF Target temperature: 70° C., a Temperature Ramp Rate: 10° C./min, a Procedure Duration: 7:30 min, and a Maximum Power: 20 W.

Test Media may include fresh chicken breast. Sample preparation may include the chicken breast being immersed in hot water to reach 37° C., and thereafter placing the warmed test tissue between two acrylic plates. This setup may facilitate visualization of lesion formation and also help better understand the cooperative growth of the lesions.

The formation of lesions in the test tissue under the parameters discussed above and according to the probe positions discussed below can be recorded using photographic and/or radiographic processes. The set-up and results of the tests are depicted in FIGS. 6A-19.

Probes are inserted into the test tissue with a relative angle (θ) of 75° between the probes, as depicted in FIGS. 7A, 8A, 9A, 10A, 11A, 12A, 13A, 14A, and 15A. As provided above, probe tip distance deltas Δx may vary, as illustrated by FIGS. 7A, 8A, 9A, 10A, 11A, 12A, 13A, 14A, and 15A. 75° may represent an example of an angle (θ) between the pedicles of a typical vertebra.

Figure 6A:
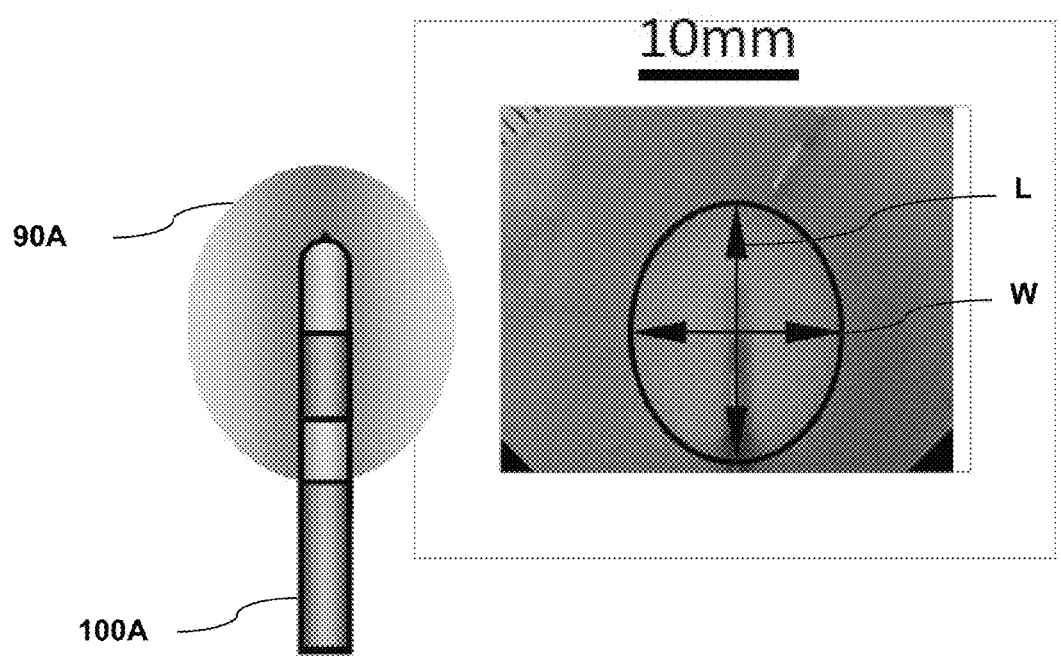
FIG. 6A illustrates a top schematic view of the first bipolar probe and a lesion formed thereby, and includes a top radiographic view of the positioning of the distal end of the first bipolar probe having an active distal end length of 10 mm and showing an overlay depicting a length and width of a lesion formed thereby.
Figure 6B:
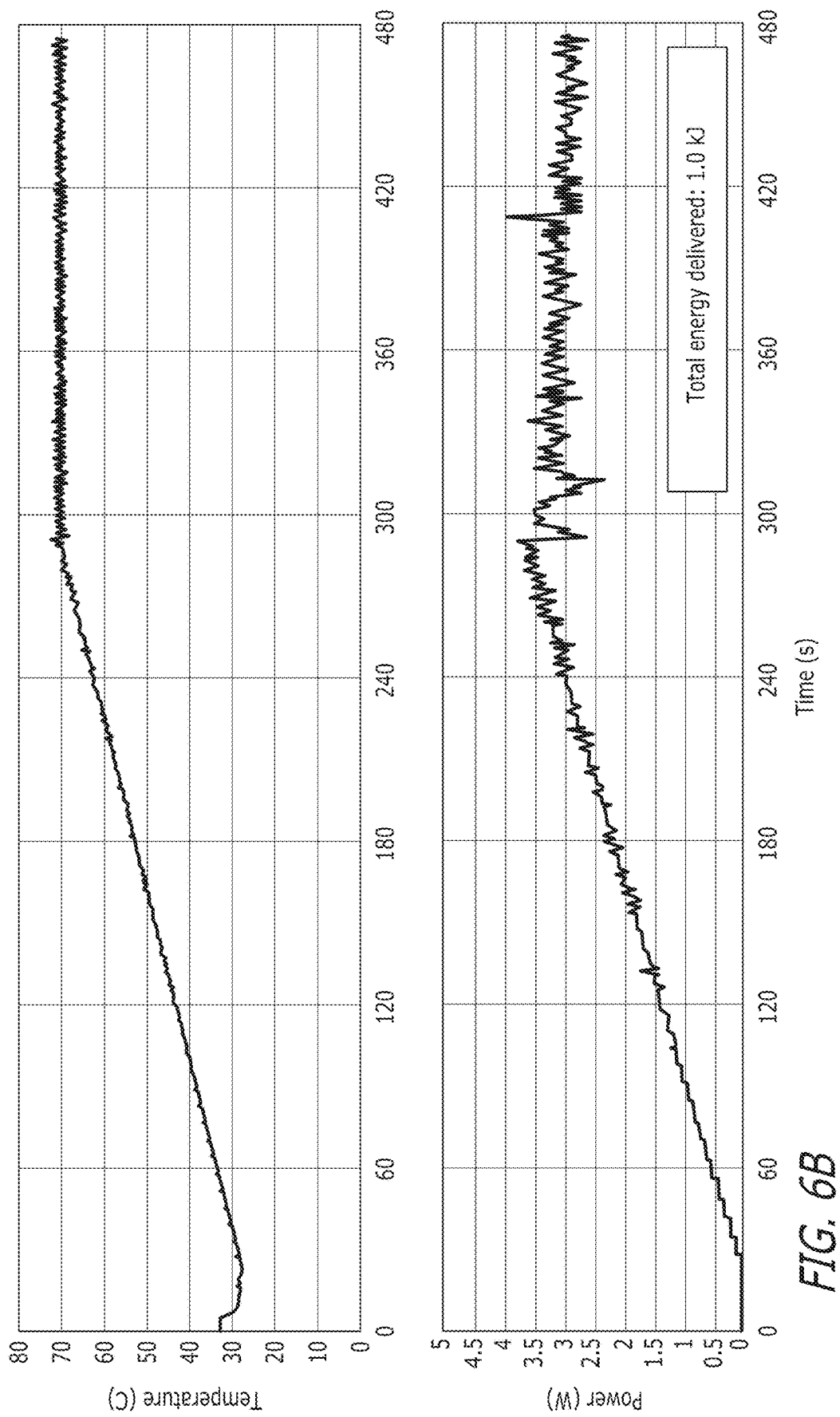
FIG. 6B illustrates temperature and power graphs of the first bipolar probe during use thereof according to the distal end position of FIG. 6A.

Formation of a single lesion using a single probe 100A, as depicted in FIG. 6A, may be measured as a reference during testing. L (16 mm) and W (13 mm) denote lesion length and width, respectively, as shown in FIG. 6A. FIG. 6B illustrates temperature and power graphs of the probe 100A resulting from use thereof, where the area under the power-time graph yields the total energy delivered to tissue during an ablation procedure. A second probe's thermocouple may be used to identify the boundary of an ablation zone where the temperature remains around 45-50° C.

Figure 7A:
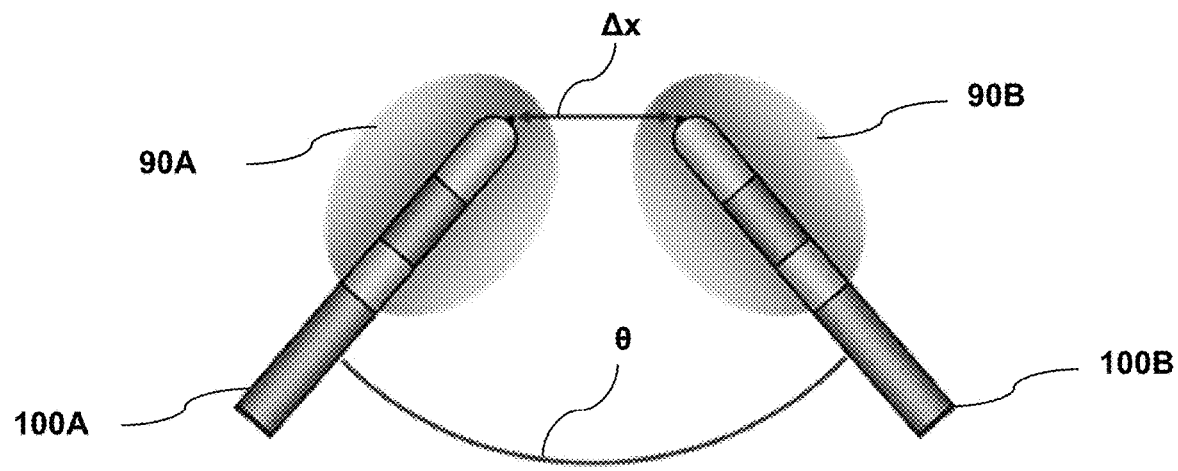
FIG. 7A illustrates a top schematic view of the positioning the distal ends of the first and second bipolar probes including a probe tip distance delta of 24 mm.
Figure 7B:
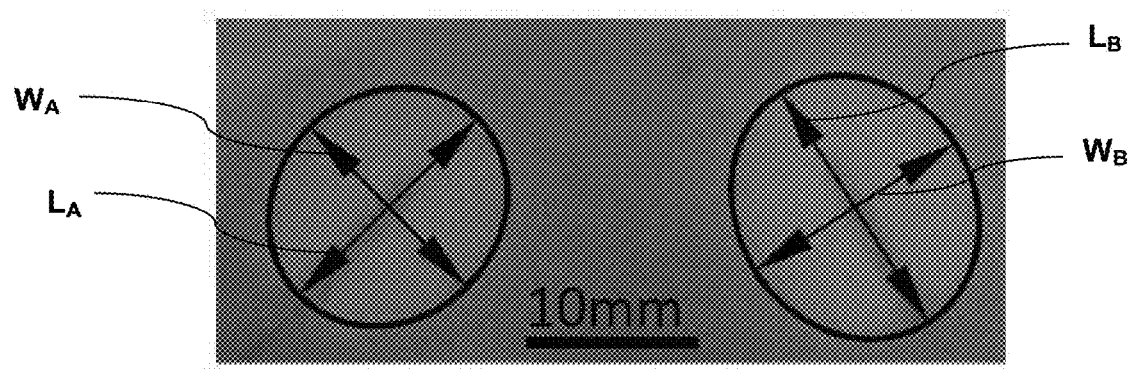
FIG. 7B is a top radiographic view of the positioning of the first and second bipolar probes having active distal end lengths of 10 mm and corresponding to FIG. 7A, and showing an overlay depicting lengths and widths of respective lesions formed thereby.
Figure 7C:
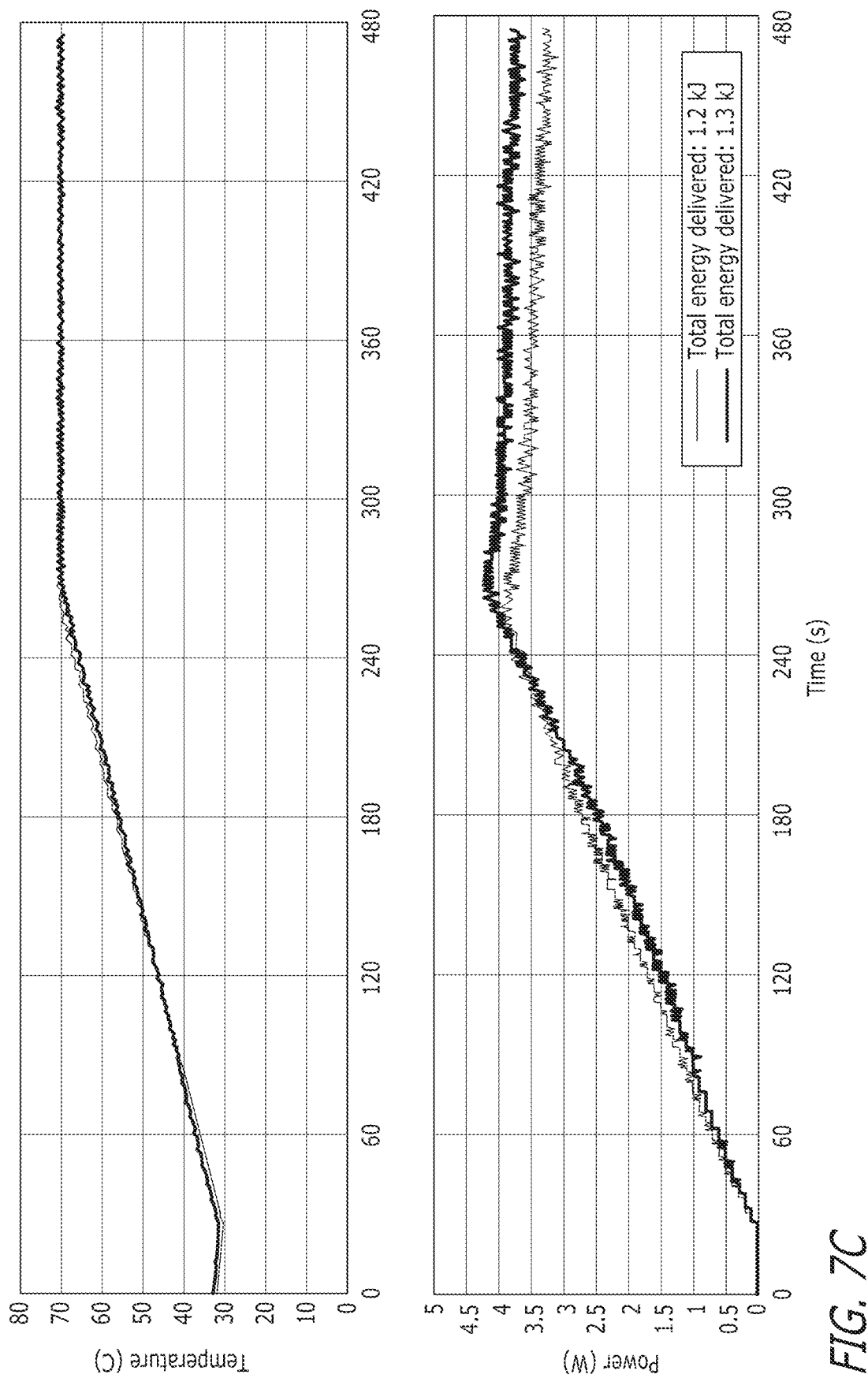
FIG. 7C illustrates temperature and power graphs of the first and second bipolar probes during use thereof according to the distal end positions of FIGS. 7A and 7B and the probe tip distance delta of 24 mm.

FIGS. 7A-7C illustrate a probe tip distance delta Δx of 24 mm and corresponding lesion lengths ($L_A$=15 mm and $L_B$=16 mm) and lesion widths ($W_A$=13 mm and $W_B$=14 mm), and temperature and power graphs resulting from use of the bipolar probes 100A, 100B.

Figure 8A:
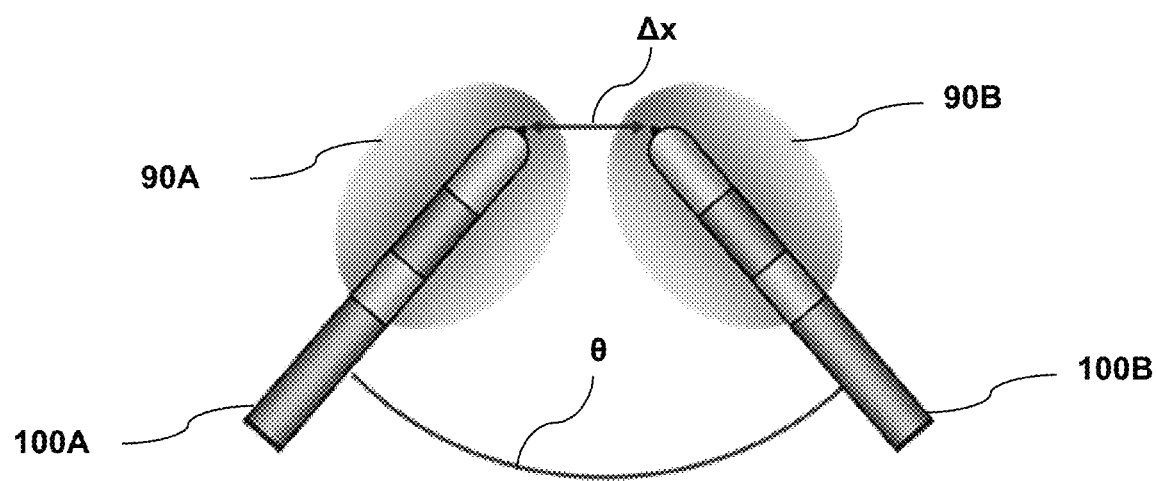
FIG. 8A illustrates a top schematic view of the positioning of the distal ends of the first and second bipolar probes including a probe tip distance delta of 16 mm.
Figure 8B:
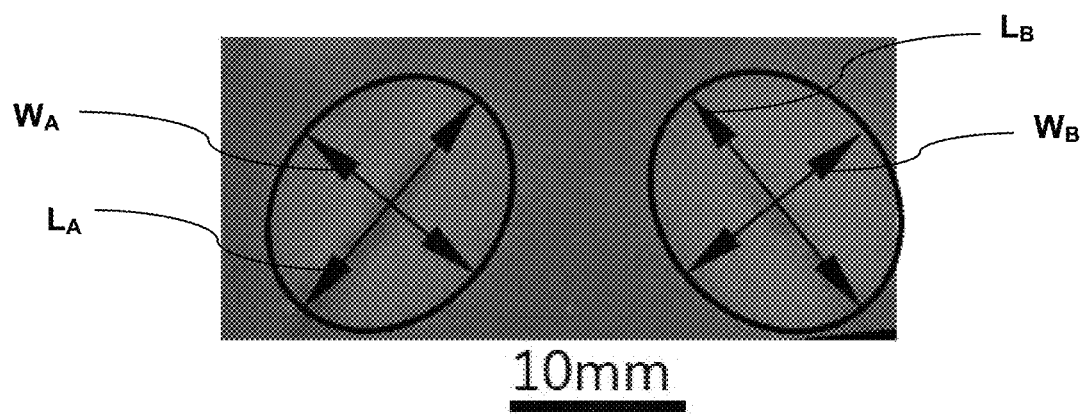
FIG. 8B is a top radiographic view of the positioning of the first and second bipolar probes having active distal end lengths of 10 mm and corresponding to FIG. 8A, and showing an overlay depicting lengths and widths of respective lesions formed thereby.
Figure 8C:
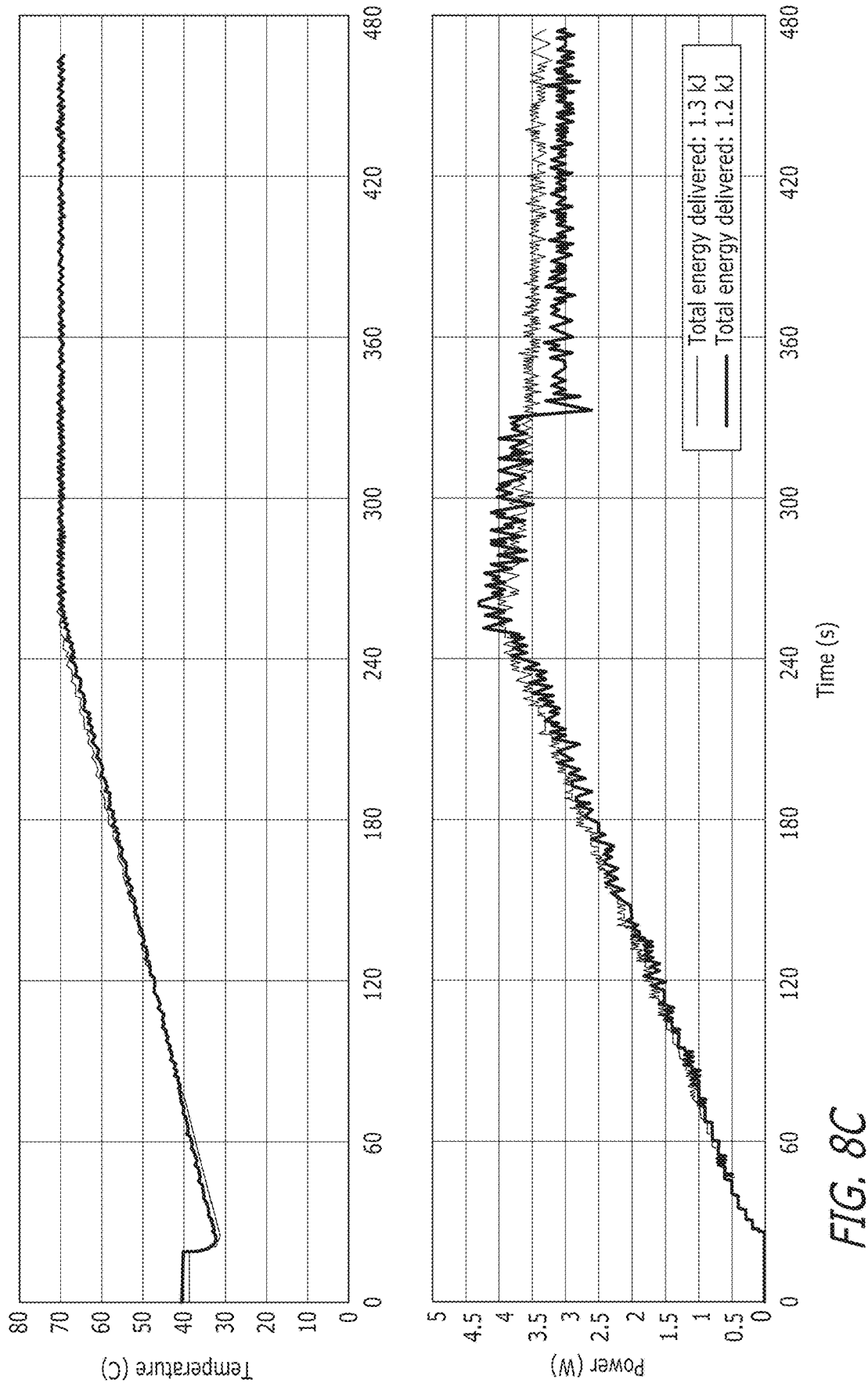
FIG. 8C illustrates temperature and power graphs of the first and second bipolar probes during use thereof according to the distal end positions of FIGS. 8A and 8B and the probe tip distance delta of 16 mm.

FIGS. 8A-8C illustrate a probe tip distance delta Δx of 16 mm and corresponding lesion lengths ($L_A$=16 mm and $L_B$=16 mm) and lesion widths ($W_A$=13 mm and $W_B$=13 mm), and temperature and power graphs resulting from use of the bipolar probes 100A, 100B.

Figure 9A:
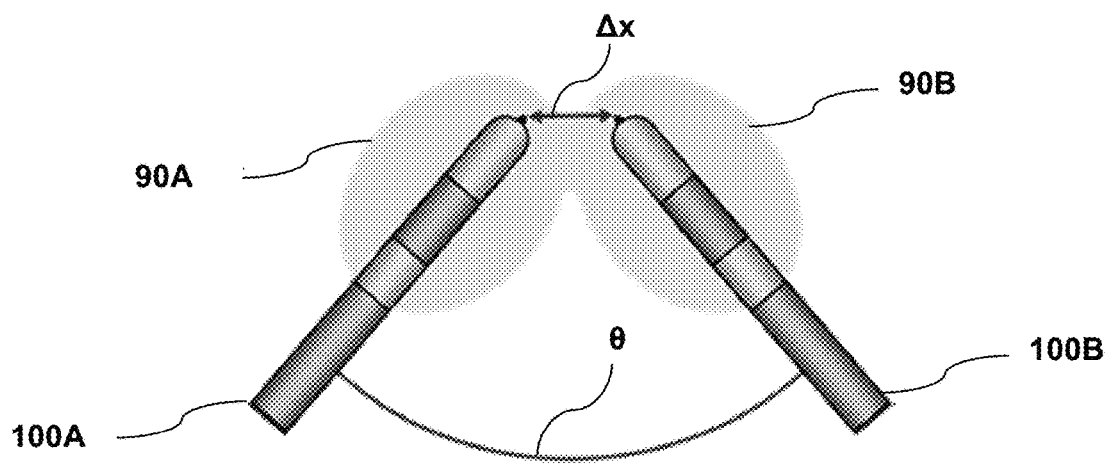
FIG. 9A illustrates a top schematic view of the positioning of the distal ends of the first and second bipolar probes including a probe tip distance delta of 12 mm.
Figure 9B:
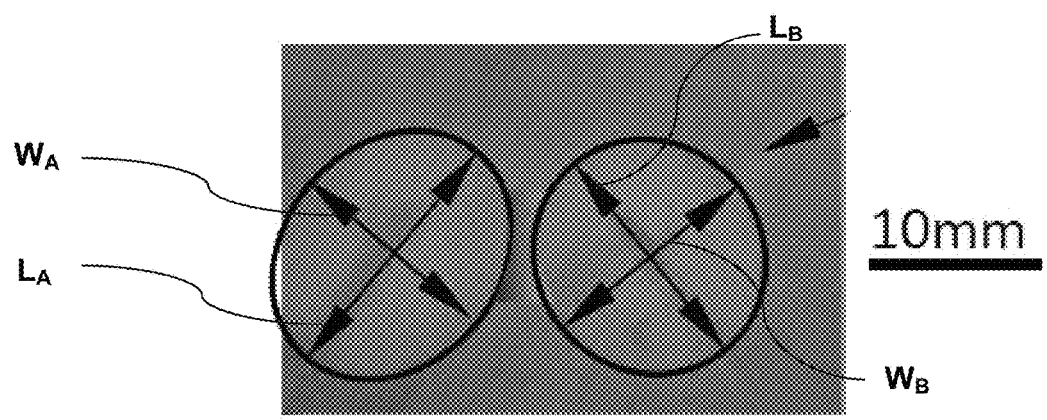
FIG. 9B is a top radiographic view of the positioning of the first and second bipolar probes having active distal end lengths of 10 mm and corresponding to FIG. 9A, and showing an overlay depicting lengths and widths of respective lesions formed thereby.
Figure 9C:
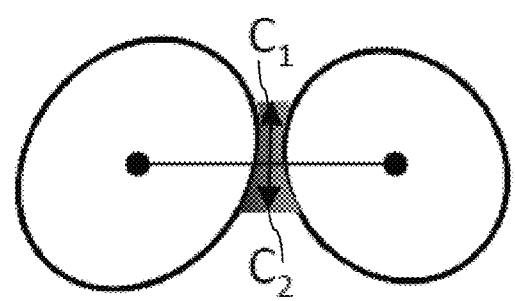
FIG. 9C illustrates an extra area that may be ablated due to thermal interaction between the lesions formed by the first and second bipolar probes.
Figure 9D:
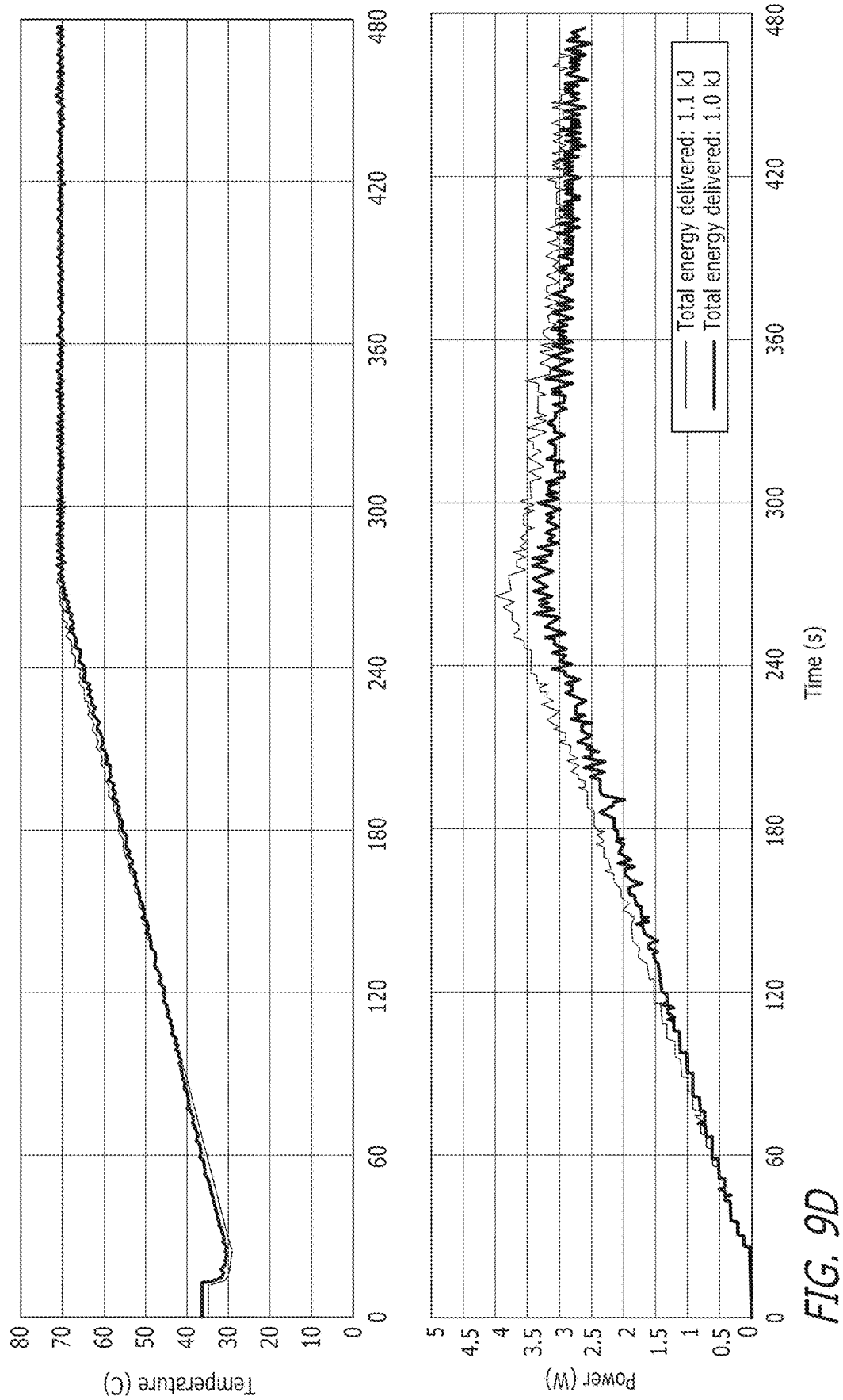
FIG. 9D illustrates temperature and power graphs of the first and second bipolar probes during use thereof according to the distal end positions of FIGS. 9A and 9B and the probe tip distance delta of 12 mm.
Figure 10A:
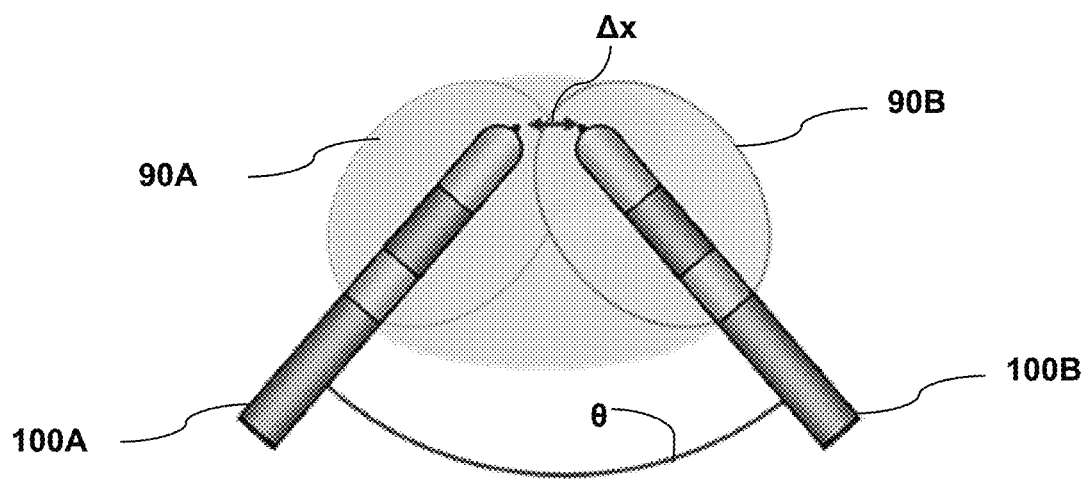
FIG. 10A illustrates a top schematic view of the positioning of the distal ends of the first and second bipolar probes including a probe tip distance delta of 8 mm.
Figure 10B:
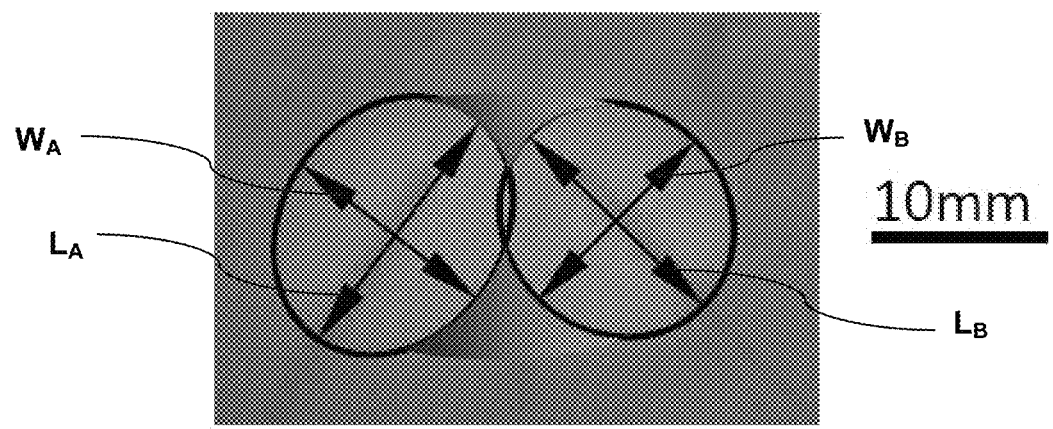
FIG. 10B is a top radiographic view of the positioning of the first and second bipolar probes having active distal end lengths of 10 mm and corresponding to FIG. 10A, and showing an overlay depicting lengths and widths of respective lesions formed thereby.
Figure 10C:
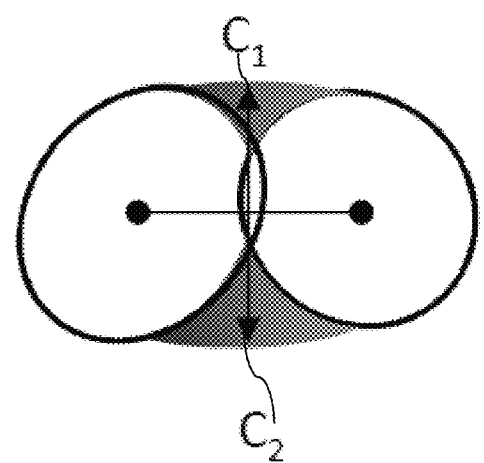
FIG. 10C illustrates an extra area that may be ablated due to thermal interaction between the lesions formed by the first and second bipolar probes.
Figure 10D:
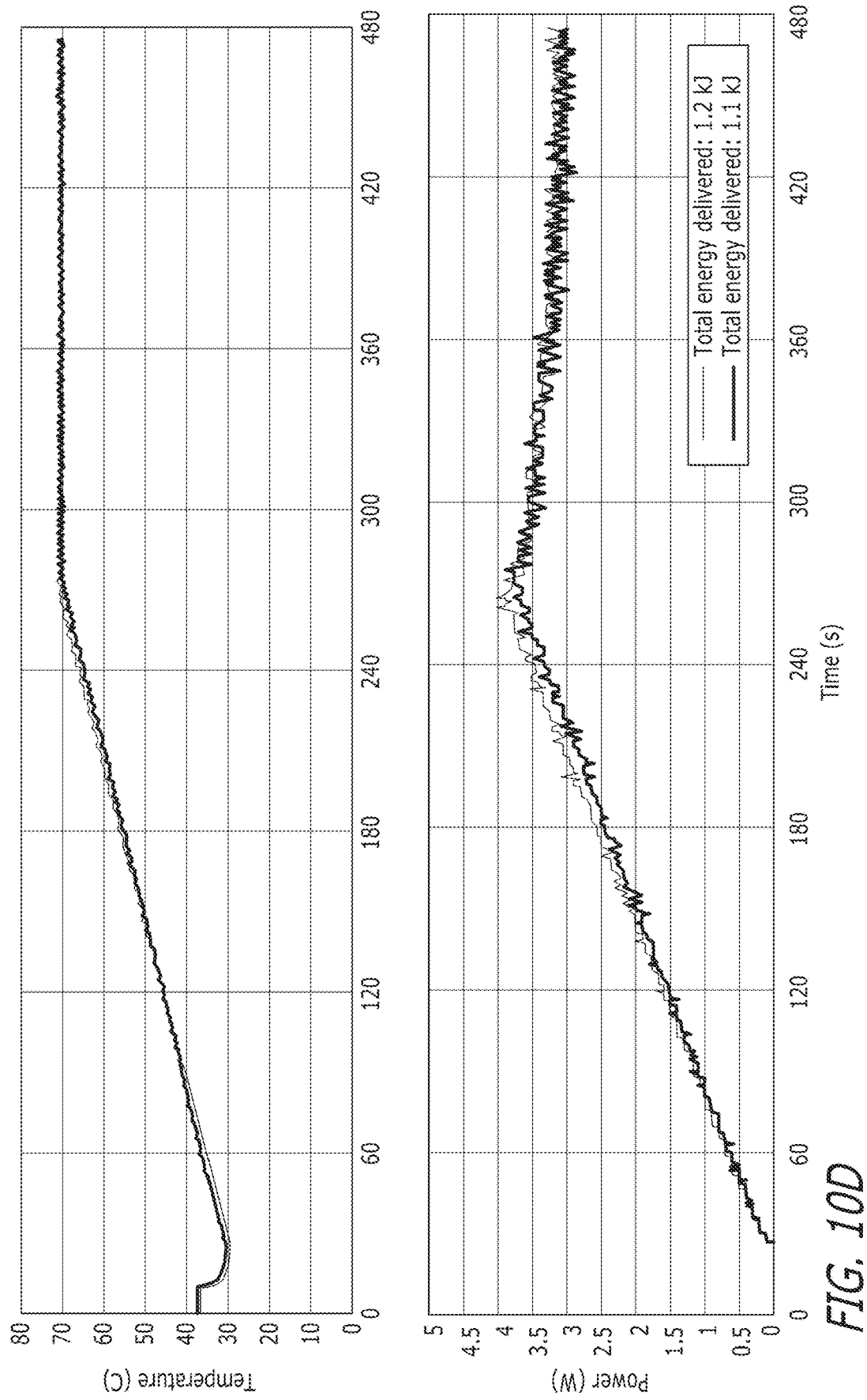
FIG. 10D illustrates temperature and power graphs of the first and second bipolar probes during use thereof according to the distal end positions of FIGS. 10A and 10B and the probe tip distance delta of 8 mm.
Figure 11A:
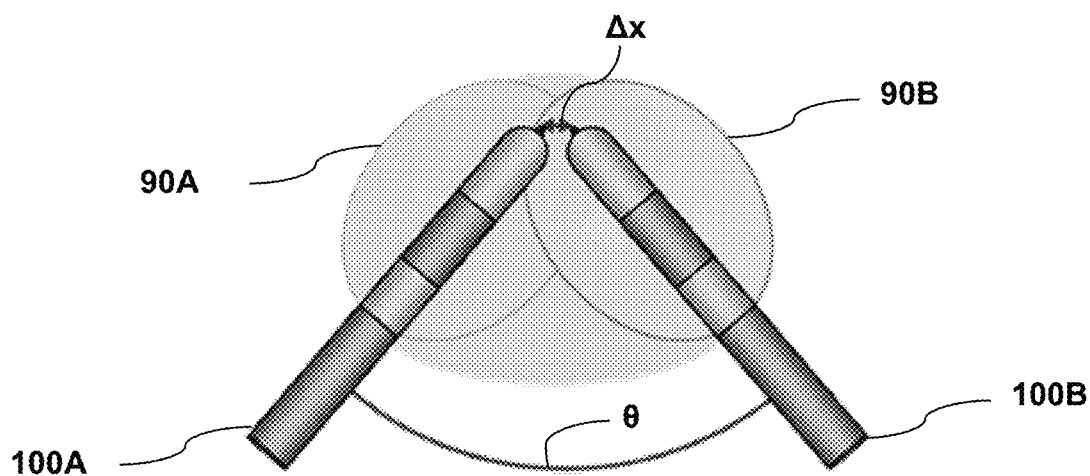
FIG. 11A illustrates a top schematic view of the positioning of the distal ends of the first and second bipolar probes including a probe tip distance delta of 4 mm.
Figure 11B:
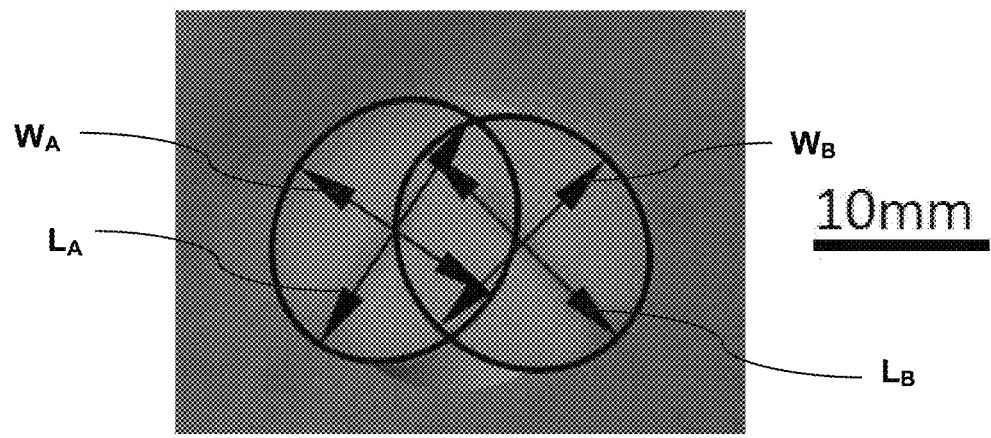
FIG. 11B is a top radiographic view of the positioning of the first and second bipolar probes having active distal end lengths of 10 mm and corresponding to FIG. 11A, and showing an overlay depicting lengths and widths of respective lesions formed thereby.
Figure 11C:
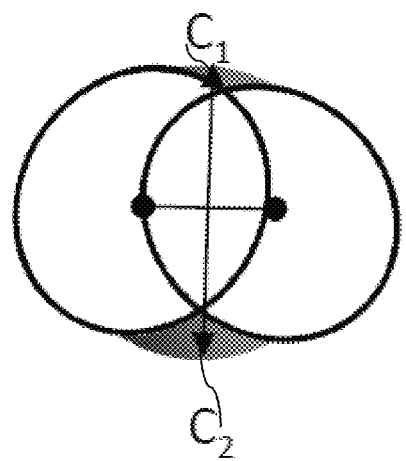
FIG. 11C illustrates an extra area that may be ablated due to thermal interaction between the lesions formed by the first and second bipolar probes.
Figure 11D:
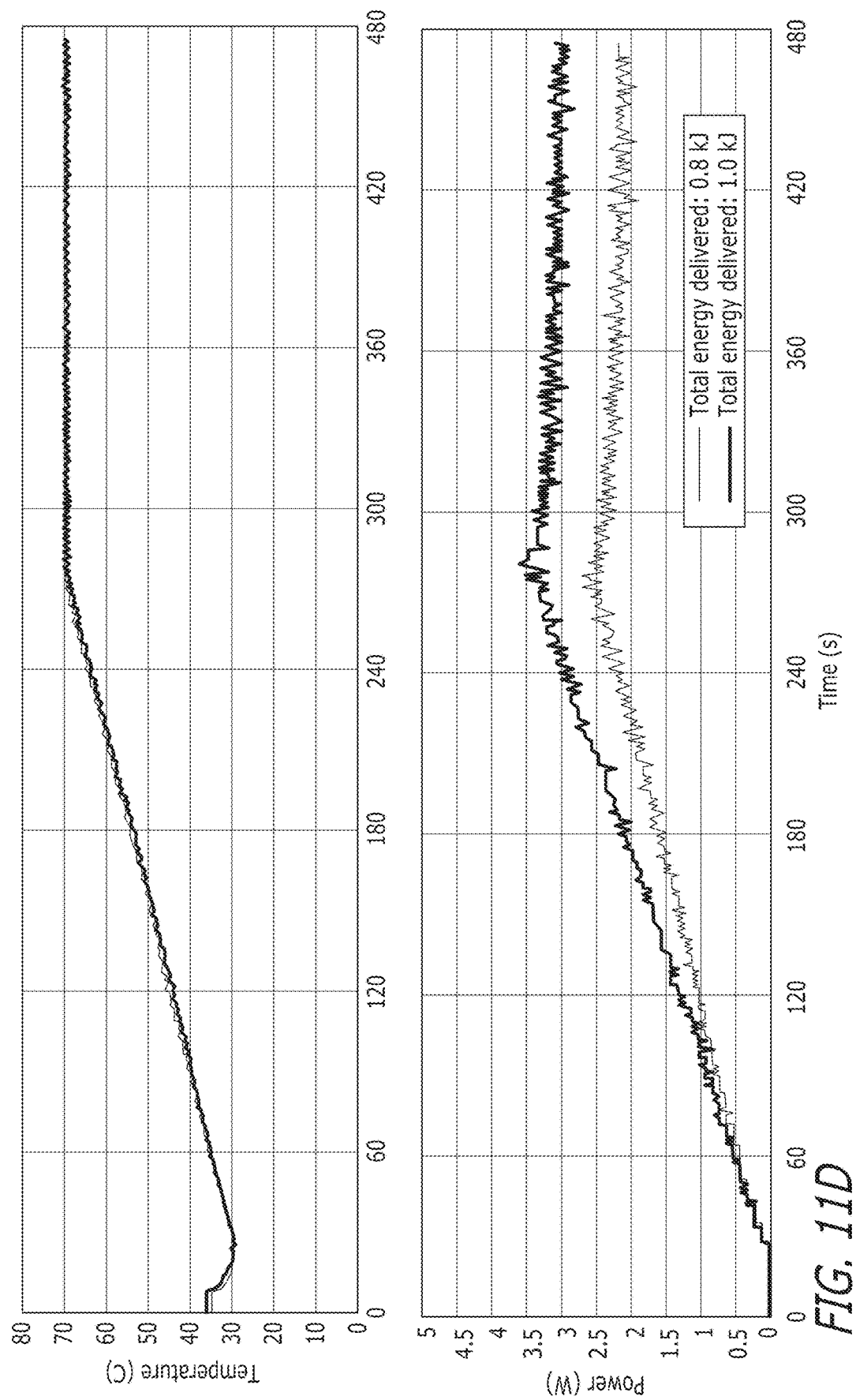
FIG. 11D illustrates temperature and power graphs of the first and second bipolar probes during use thereof according to the distal end positions of FIGS. 11A and 11B and the probe tip distance delta of 4 mm.
Figure 12A:
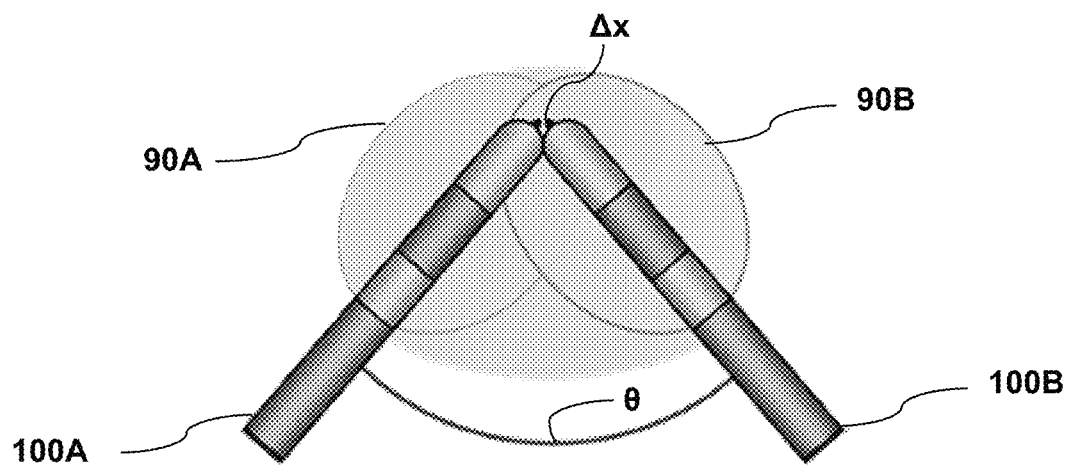
FIG. 12A illustrates a top schematic view of the positioning of the distal ends of the first and second bipolar probes including a probe tip distance delta of 0 mm.
Figure 12B:
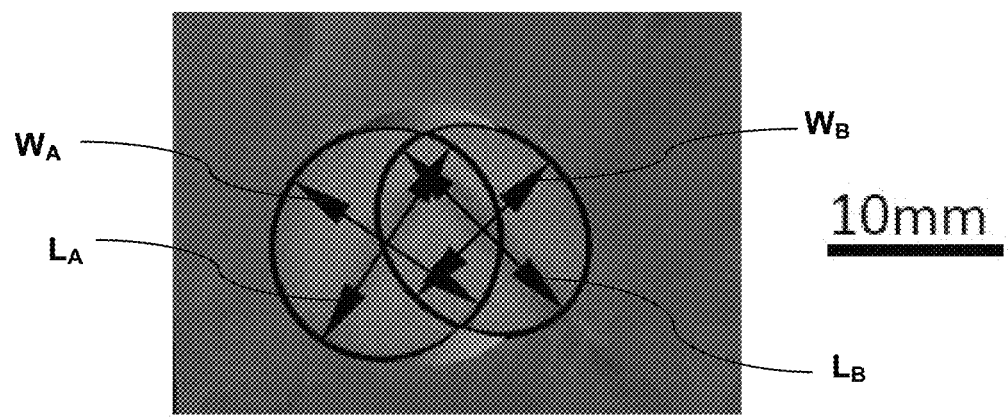
FIG. 12B is a top radiographic view of the positioning of the first and second bipolar probes having active distal end lengths of 10 mm and corresponding to FIG. 12A, and showing an overlay depicting lengths and widths of respective lesions formed thereby.
Figure 12C:
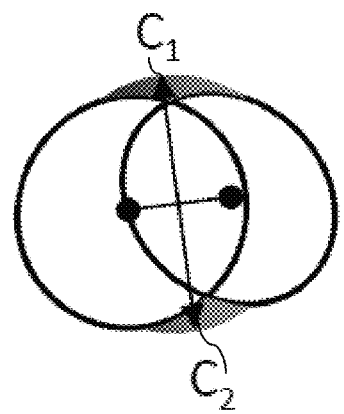
FIG. 12C illustrates an extra area that may be ablated due to thermal interaction between the lesions formed by the first and second bipolar probes.
Figure 12D:
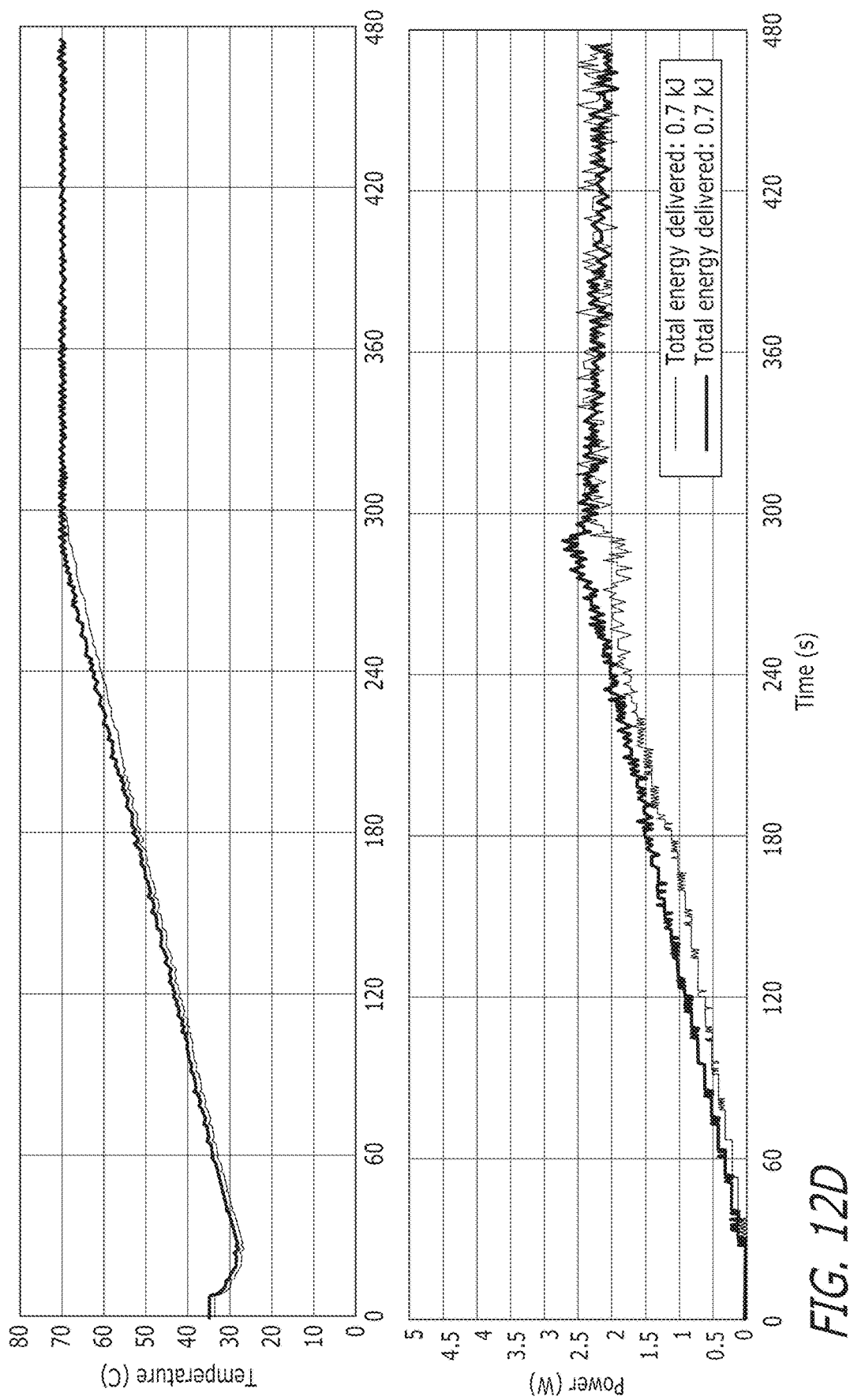
FIG. 12D illustrates temperature and power graphs of the first and second bipolar probes during use thereof according to the distal end positions of FIGS. 12A and 12B and the probe tip distance delta of 0 mm.
Figure 13A:
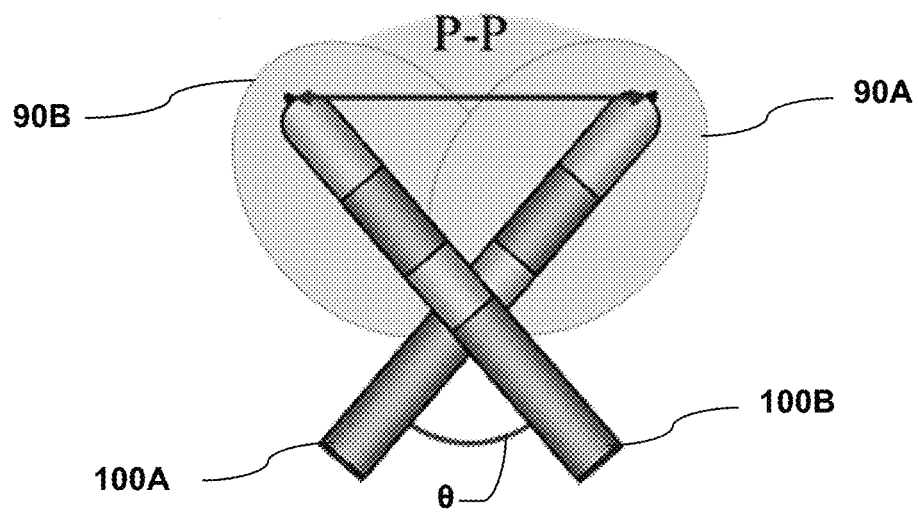
FIG. 13A illustrates a top schematic view of the positioning of the distal ends of the first and second bipolar probes crossing and touching one another.
Figure 13B:
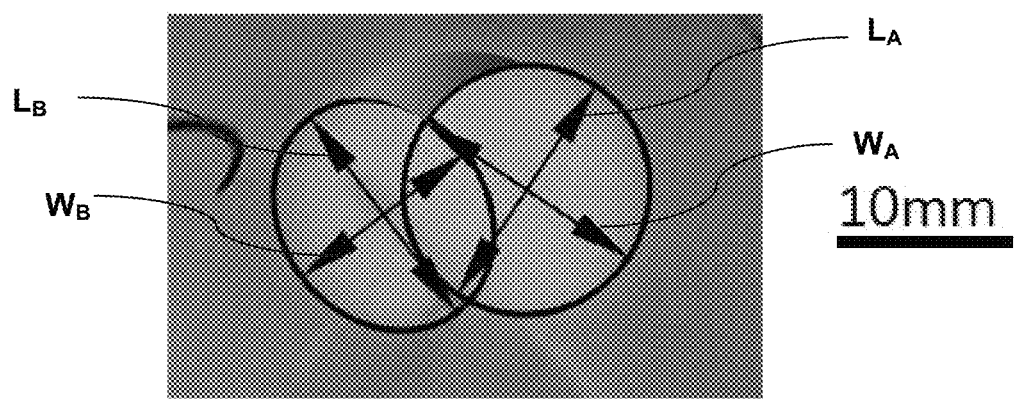
FIG. 13B is a top radiographic view of the positioning of the first and second bipolar probes having active distal end lengths of 10 mm and corresponding to FIG. 13A, and showing an overlay depicting lengths and widths of respective lesions formed thereby.
Figure 13C:
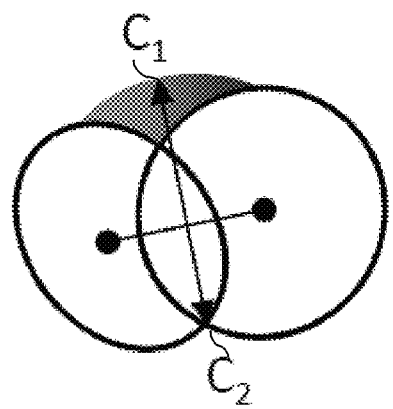
FIG. 13C illustrates an extra area that may be ablated due to thermal interaction between the lesions formed by the first and second bipolar probes.
Figure 13D:
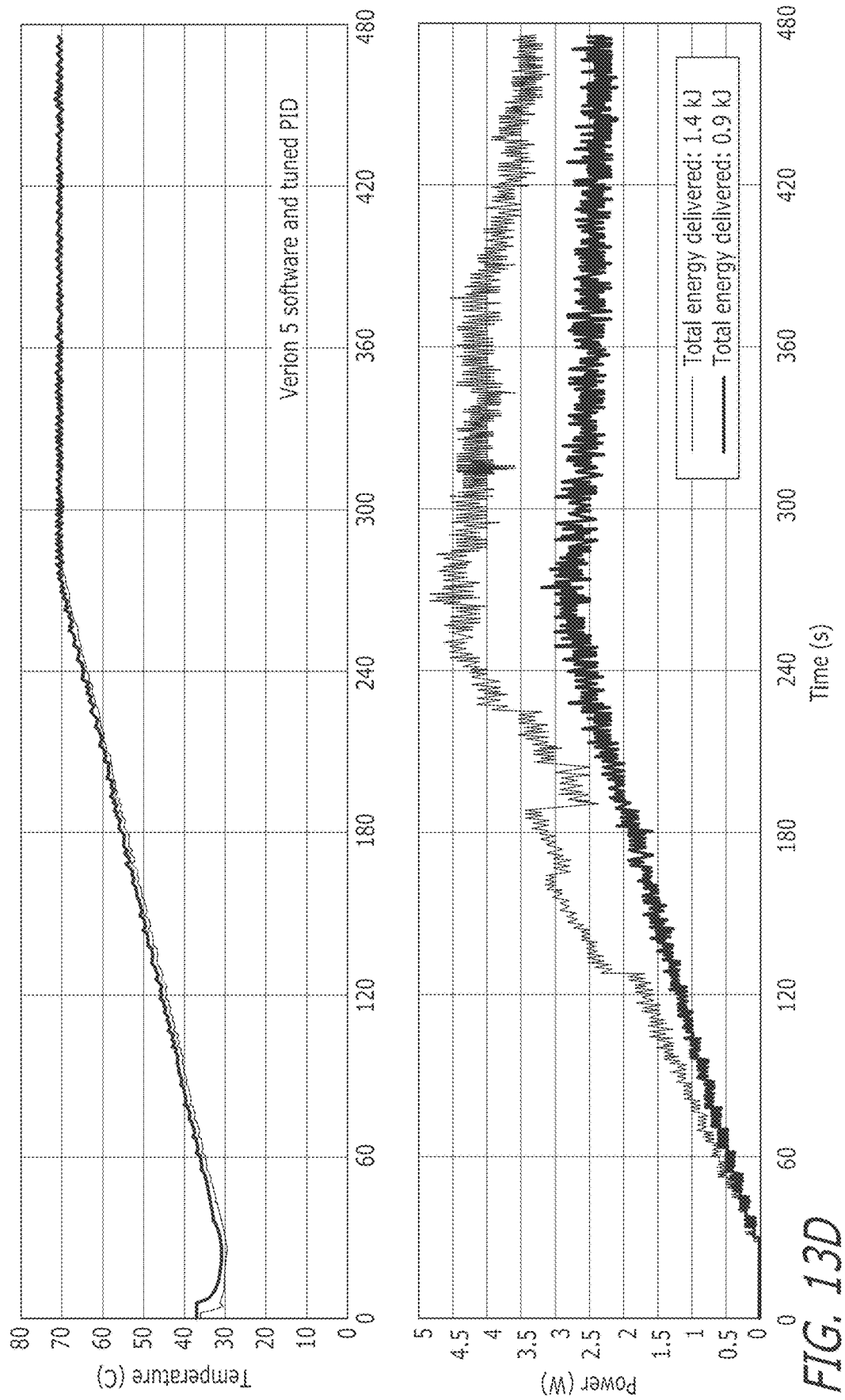
FIG. 13D illustrates temperature and power graphs of the first and second bipolar probes during use thereof according to the distal end positions of FIGS. 13A and 13B.

FIGS. 9A-9D illustrate a probe tip distance delta Δx of 12 mm and corresponding lesion lengths ($L_A$=16 mm and $L_B$=14 mm) and lesion widths ($W_A$=13 mm and $W_B$=13 mm), and temperature and power graphs resulting from use of the bipolar probes 100A, 100B. FIG. 9C further illustrates an extra area or areas that may be ablated due to the thermal interaction of the two lesions. Parameter C (e.g., $C_1$ and $C_2$) is the distance between the line connecting the centers of the two lesions and the boundaries of the extra ablated area. $C_1$ is the distance between the line connecting the centers of the two lesions and the top of the extra ablated area, as shown in FIG. 9C. $C_2$ is the distance between the line connecting the centers of the two lesions and the bottom of the extra ablated area, as shown in FIG. 9C. According to the orientation of FIG. 9C, this understanding for $C_1$ and $C_2$ is generally applicable to FIGS. 10C, 11C, 12C, 13C, 14C, 18, 19, and 20.

FIGS. 10A-10D illustrate a probe tip distance delta Δx of 8 mm and corresponding lesion lengths ($L_A$=16 mm and $L_B$=14 mm) and lesion widths ($W_A$=13 mm and $W_B$=13 mm), extra areas formed by the thermal interaction of the two lesions, and temperature and power graphs resulting from use of the bipolar probes 100A, 100B.

FIGS. 11A-11D illustrate a probe tip distance delta Δx of 4 mm and corresponding lesion lengths ($L_A$=16 mm and $L_B$=15 mm) and lesion widths ($W_A$=13 mm and $W_B$=14 mm), extra areas formed by the thermal interaction of the two lesions, and temperature and power graphs resulting from use of the bipolar probes 100A, 100B.

FIGS. 12A-12D illustrate a probe tip distance delta Δx of 0 mm and corresponding lesion lengths ($L_A$=14 mm and $L_B$=13 mm) and lesion widths ($W_A$=13 mm and $W_B$=11 mm), extra areas formed by the thermal interaction of the two lesions, and temperature and power graphs resulting from use of the bipolar probes 100A, 100B.

FIGS. 13A-13D illustrate a probe tip distance P-P where the distal ends of the bipolar probes 100A, 100B cross and touch one another, corresponding lesion lengths ($L_A$=14 mm and $L_B$=14 mm) and lesion widths ($W_A$=14 mm and $W_B$=12 mm), extra areas formed by the thermal interaction of the two lesions, and temperature and power graphs resulting from use of the bipolar probes 100A, 100B.

Figure 14A:
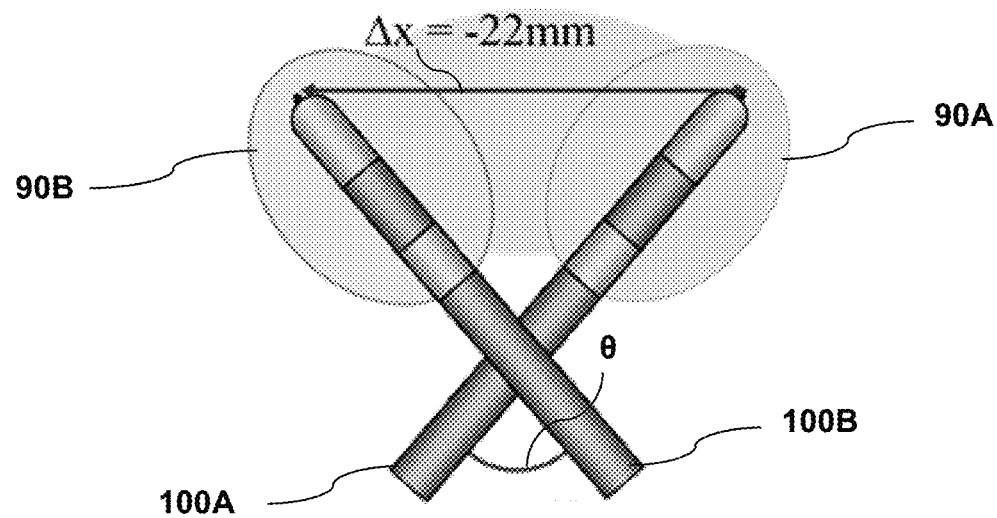
FIG. 14A illustrates a top schematic view of the positioning of the distal ends of the first and second bipolar probes including a probe tip distance delta of −22 mm.
Figure 14B:
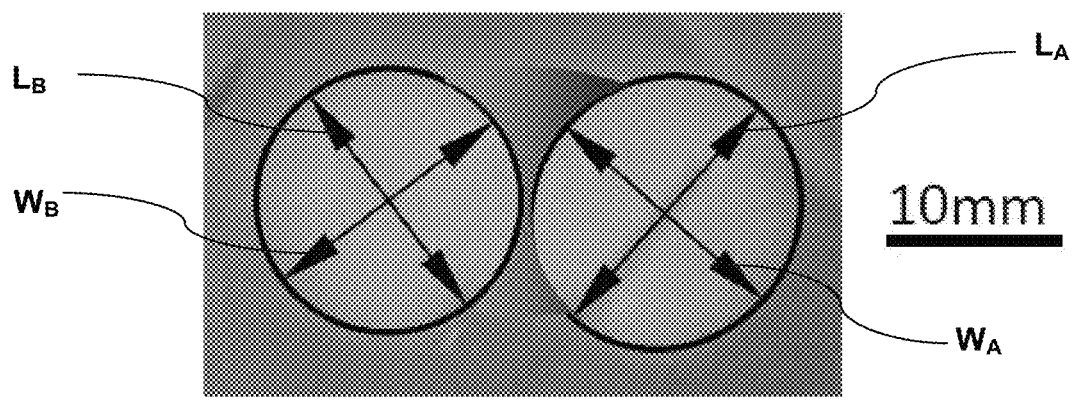
FIG. 14B is a top radiographic view of the positioning of the first and second bipolar probes having active distal end lengths of 10 mm and corresponding to FIG. 14A, and showing an overlay depicting lengths and widths of respective lesions formed thereby.
Figure 14C:
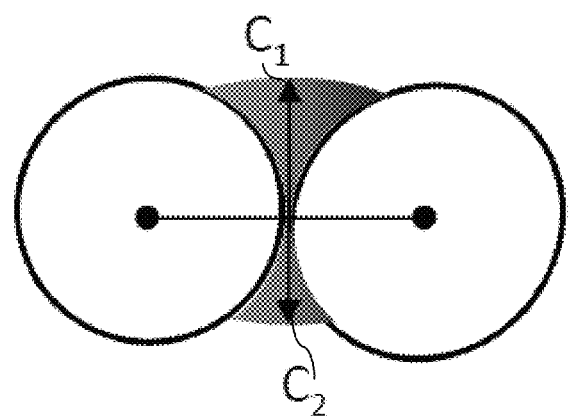
FIG. 14C illustrates an extra area that may be ablated due to thermal interaction between the lesions formed by the first and second bipolar probes.
Figure 14D:
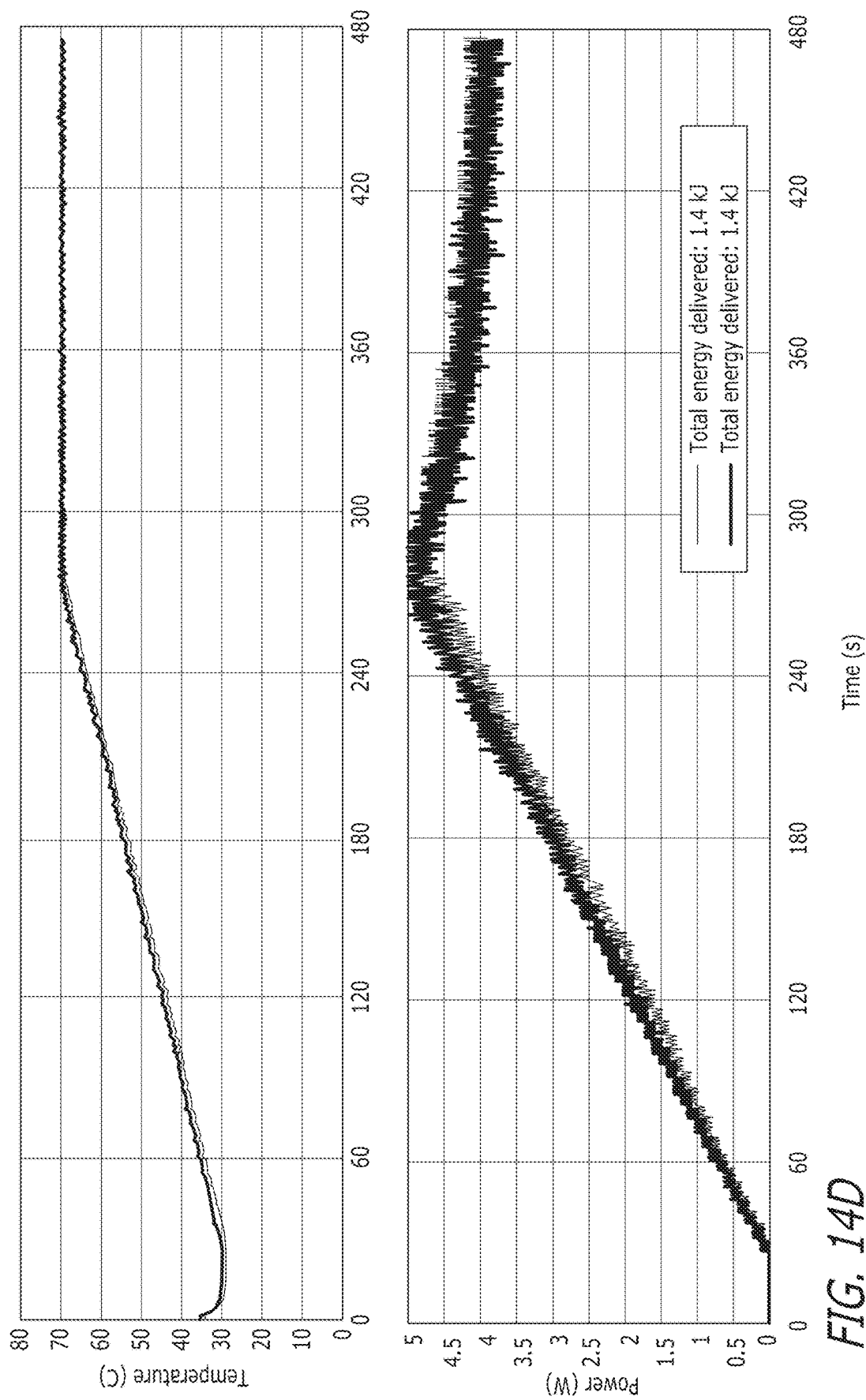
FIG. 14D illustrates temperature and power graphs of the first and second bipolar probes during use thereof according to the distal end positions of FIGS. 14A and 14B and the probe tip distance delta of −22 mm.

FIGS. 14A-14D illustrate a probe tip distance delta Δx of −22 mm and corresponding lesion lengths ($L_A$=16 mm and $L_B$=15 mm) and lesion widths ($W_A$=15 mm and $W_B$=15 mm), extra areas formed by the thermal interaction of the two lesion, and temperature and power graphs resulting from use of the bipolar probes 100A, 100B. A negative probe tip distance delta Δx indicates that the distal ends of the probes are crossing and extend past one another, as shown in FIG. 14A.

Figure 15A:
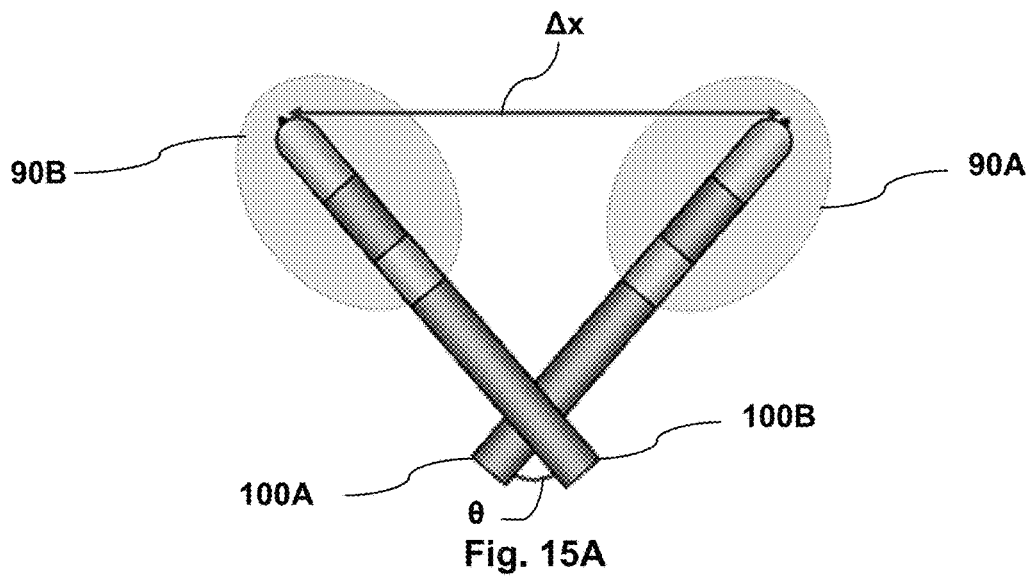
FIG. 15A illustrates a top schematic view of the positioning of the distal ends of the first and second bipolar probes including a probe tip distance delta of −30 mm.
Figure 15B:
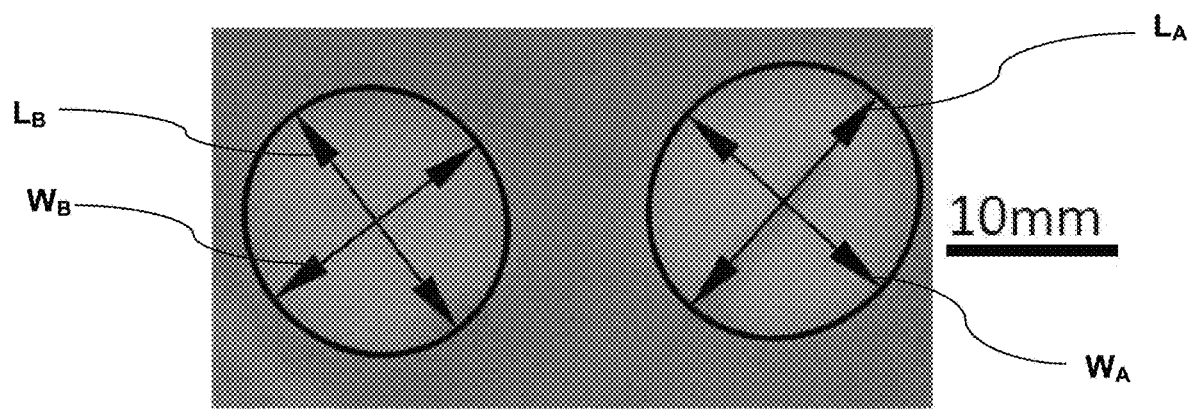
FIG. 15B is a top radiographic view of the positioning of the first and second bipolar probes having active distal end lengths of 10 mm and corresponding to FIG. 15A, and showing an overlay depicting lengths and widths of respective lesions formed thereby.
Figure 15C:
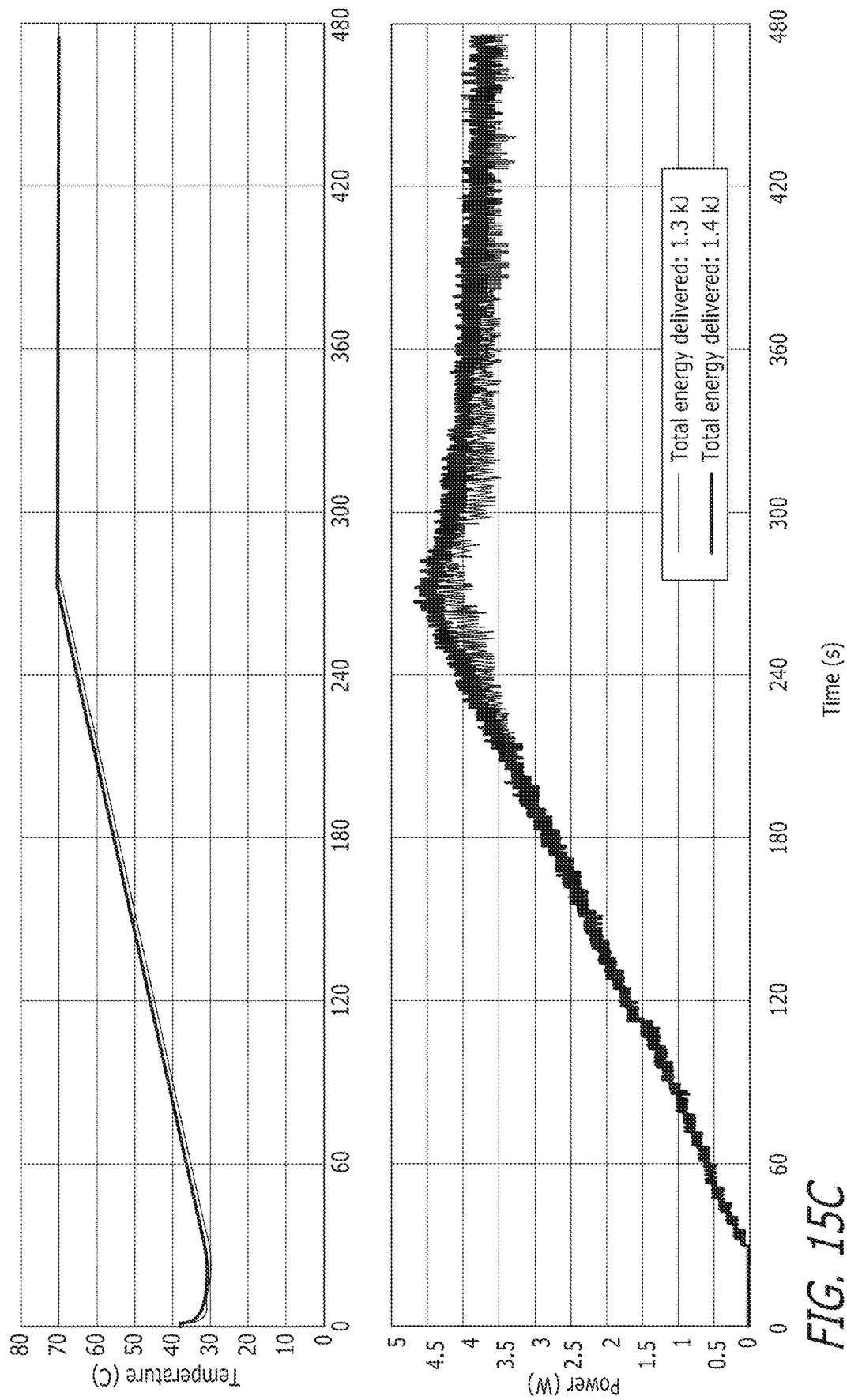
FIG. 15C illustrates temperature and power graphs of the first and second bipolar probes during use thereof according to the distal end positions of FIGS. 15A and 15B and the probe tip distance delta of −30 mm.
Figure 16:
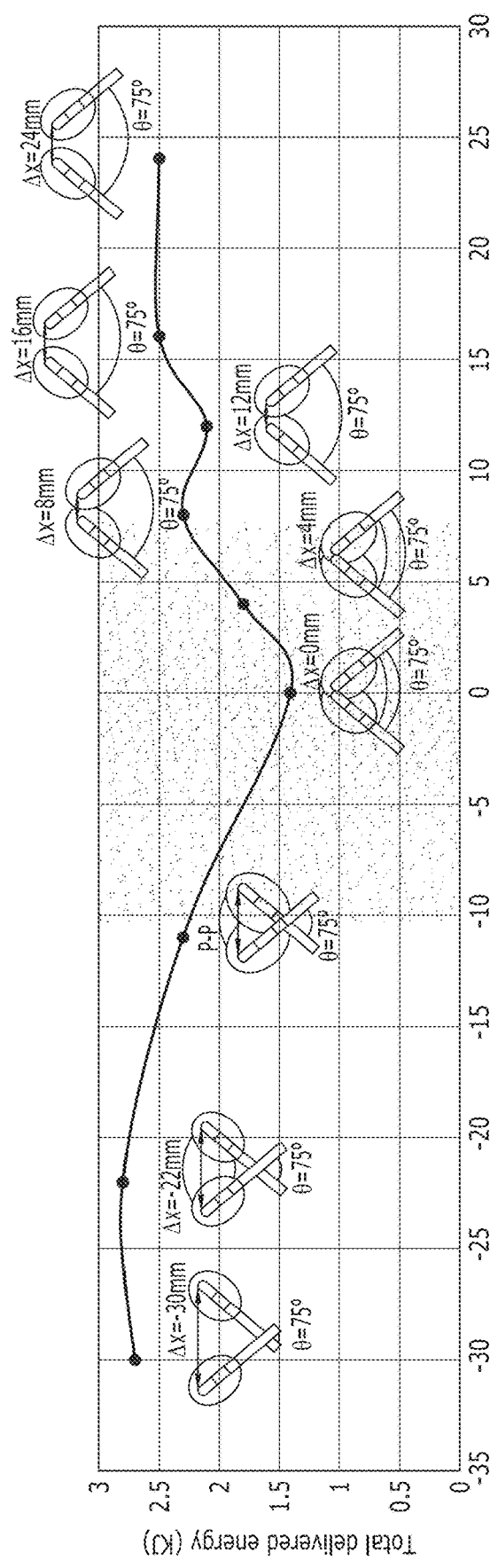
FIGS. 16-19 illustrate total delivered energy, lesion area, cooperative area, length (L), width (W), and parameter C of the first and second bipolar probes with varying distal end positions and probe tip distance deltas.
Figure 16:
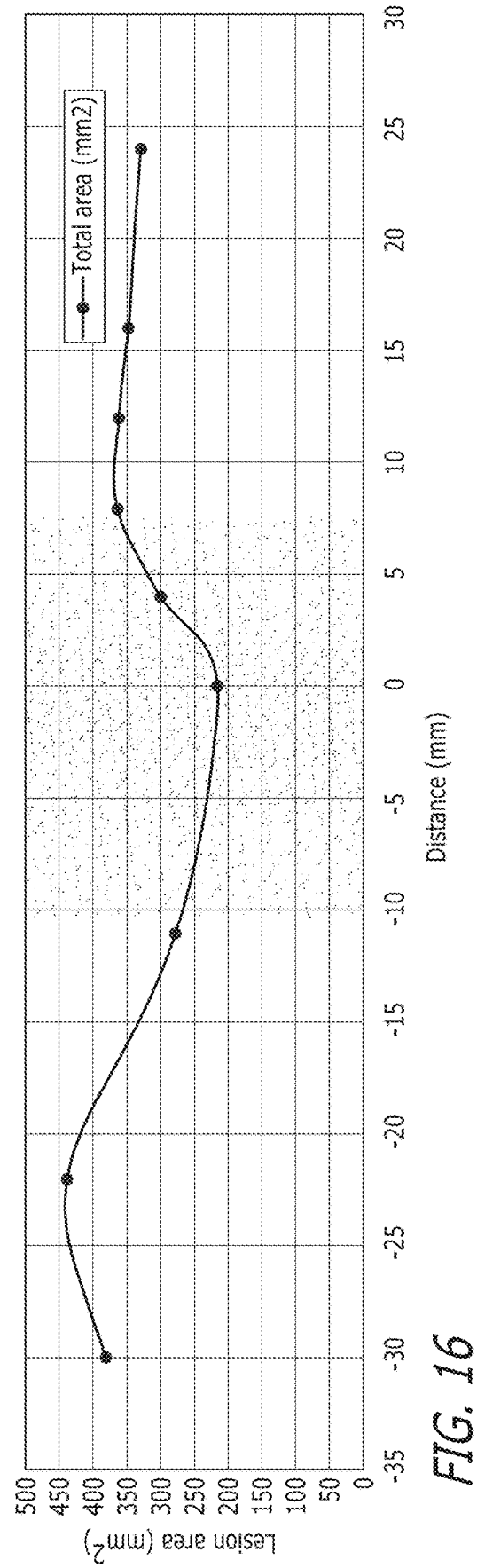
Figure 17:
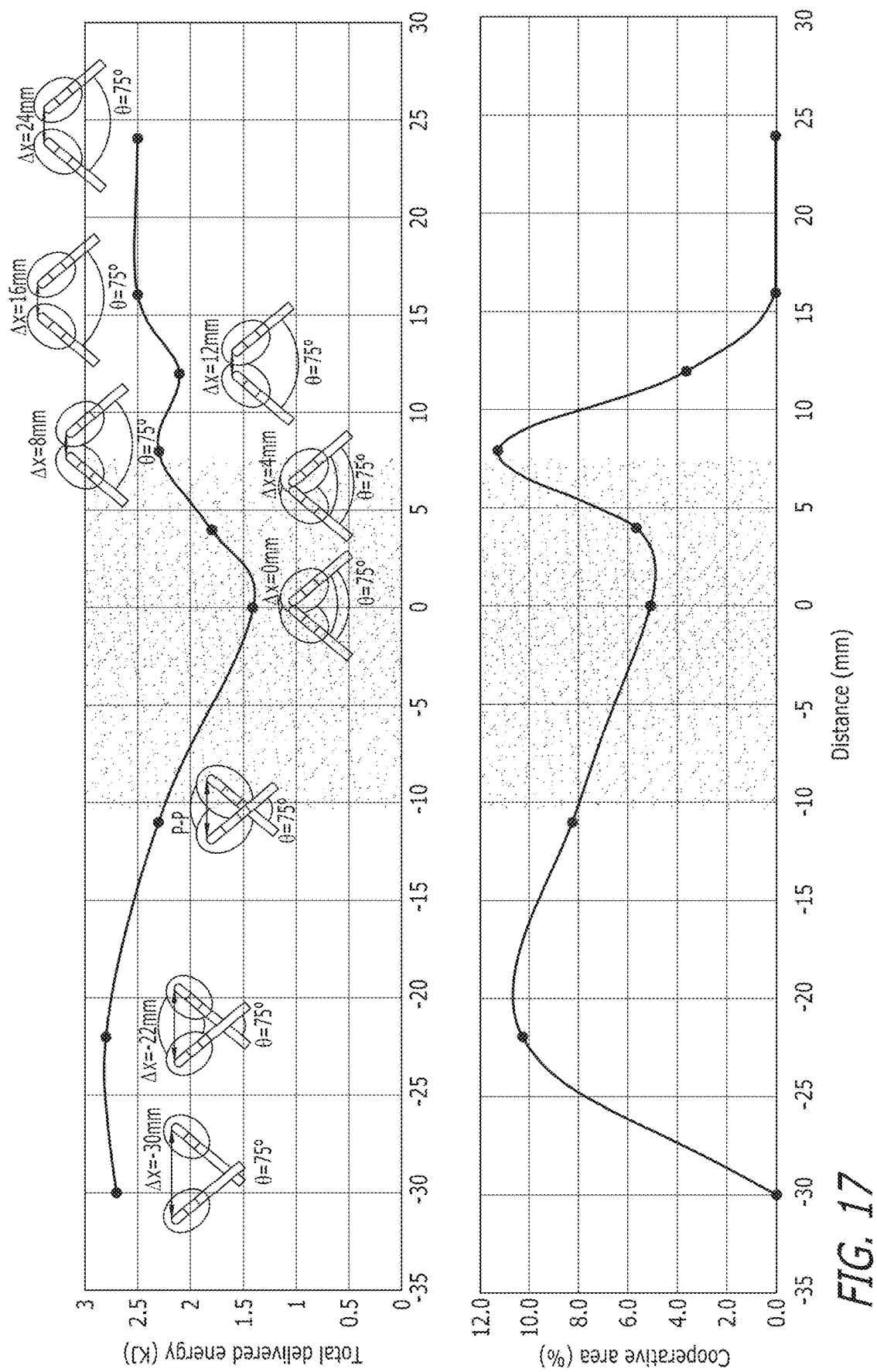
Figure 18:
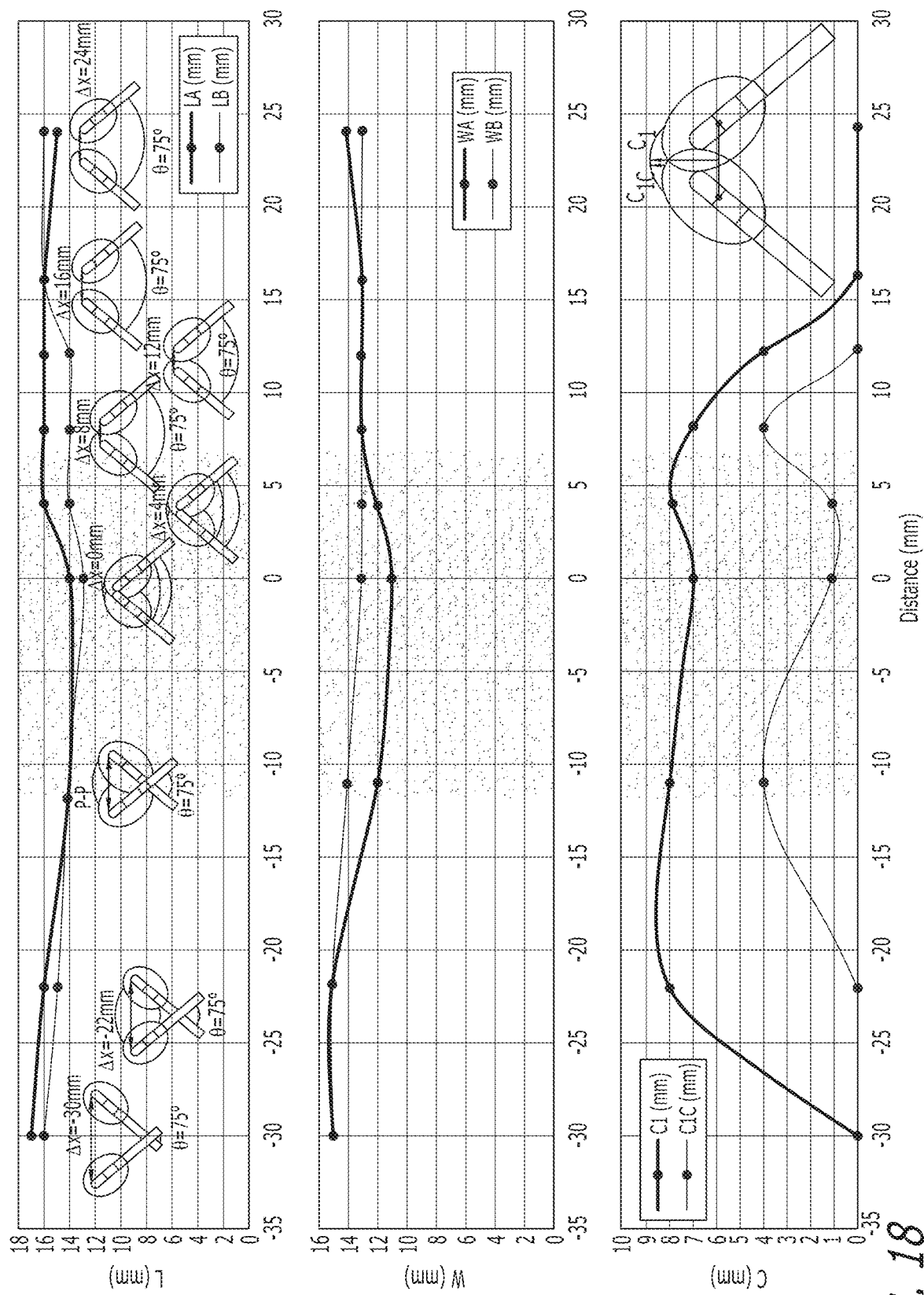
Figure 19:
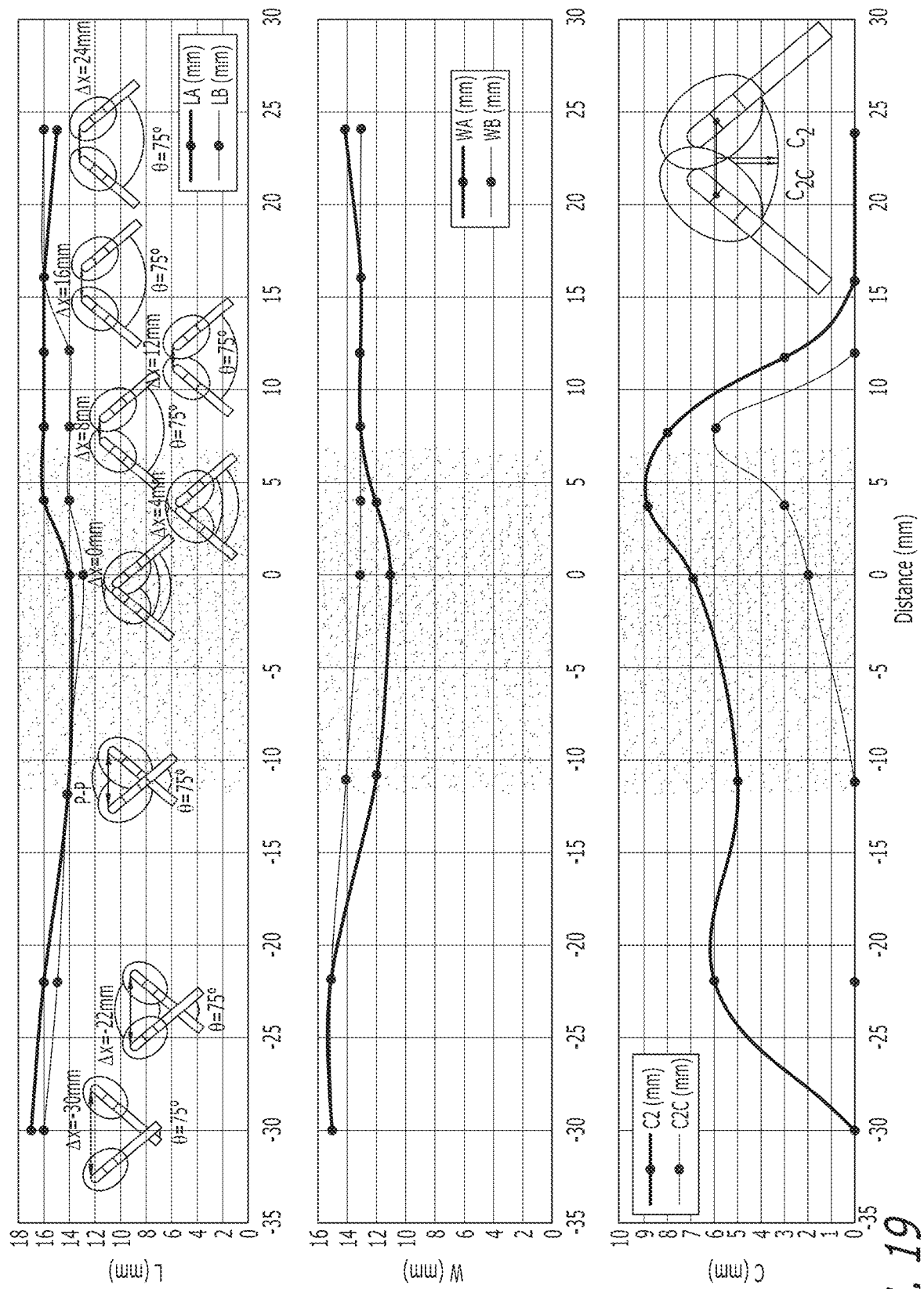

FIGS. 15A-15C illustrate a probe tip distance delta Δx of −30 mm and corresponding lesion lengths ($L_A$=17 mm and $L_B$=16 mm) and lesion widths ($W_A$=15 mm and $W_B$=15 mm), and temperature and power graphs resulting from use of the bipolar probes 100A, 100B.

FIGS. 16-19 illustrate a drop in a total lesion area that may be expected when the bipolar probes 100A, 100B are placed close to one another. An extra ablation area of up to 11% may be expected when the process includes a probe tip distance delta Δx of about 8 mm.

Figure 20:
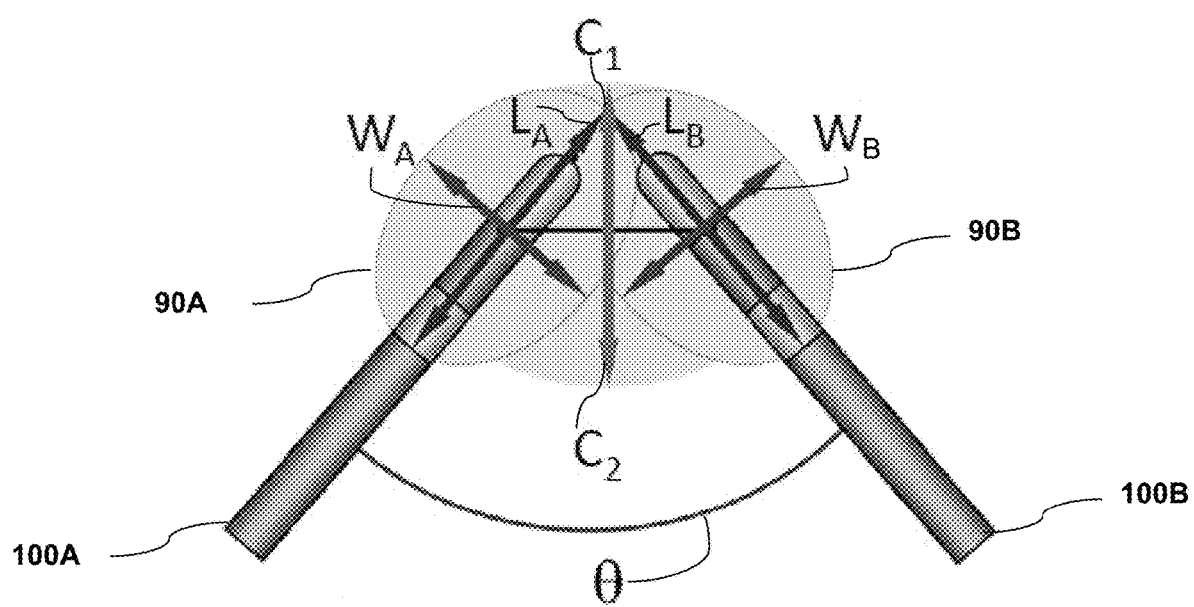
FIG. 20 illustrates another top schematic view of the first and second bipolar probes.

When the bipolar probes 100A, 100B are placed close to one another, the overall shape of the ablation zone may be characterized by six parameters: $L_A$, $W_A$, $L_B$, $W_B$, $C_1$, and $C_2$, as shown in FIG. 20.

Figure 21:
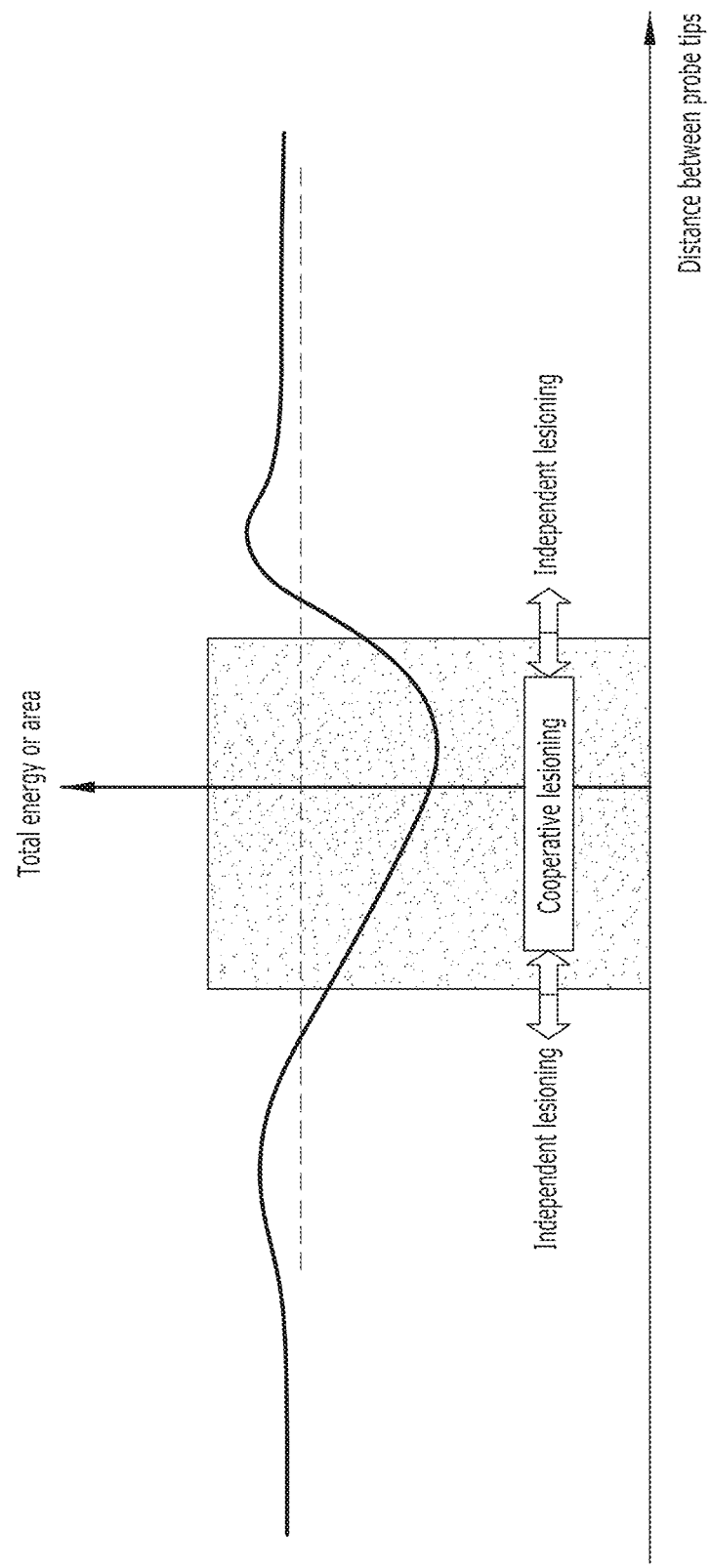
FIG. 21 illustrates a graph of total energy and probe tip distance of the first and second bipolar probes.

The total delivered energy and lesion area graphs of the bipolar probes 100A, 100B, as provided above, illustrate a minimum (due to cooperative heating/lesioning) that occurs when thermocouples of the bipolar probes 100A, 100B are placed close to one another, as shown in FIG. 21. Cooperative heating/lesioning may result in a reduction in the length and width of the lesion by up to 20%. At a particular probe distance delta Δx, an extra ablation area of 11% may result. This extra ablation area may be the result of thermal interaction between the two lesions 90A, 90B of the bipolar probes 100A, 100B.

The embodiment(s) of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications, and variations that fall within the broad scope of the appended claims. All publications, patents, and patent applications mentioned in this specification are herein incorporated in their entirety by reference into the specification, to the same extent as if each individual publication, patent, or patent application was specifically and individually indicated to be incorporated herein by reference. In addition, citation or identification of any reference in this application shall not be construed as an admission that such reference is available as prior art to the present invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of lesioning a region of a vertebral body of a patient, the method comprising:
   inserting a first bipolar probe through a first cannula positioned in a first target location in the vertebral body along a first trajectory, the first bipolar probe having a proximal end, an opposite distal end, and a first mid-longitudinal axis extending through the proximal end and the distal end thereof, the first bipolar probe including a first active tip including at least two electrodes;
   inserting a second bipolar probe through a second cannula positioned in a second target location in the vertebral body along a second trajectory, the second bipolar probe having a proximal end, an opposite distal end, and a second mid-longitudinal axis extending through the proximal end and the distal end thereof, the second bipolar probe including a second active tip including at least two electrodes;
   supplying power to the first bipolar probe;
   supplying power to the second bipolar probe independently from the supplying the power to the first bipolar probe, and
   selectively positioning the first active tip of the first bipolar probe and the second active tip of the second bipolar probe relative to one another in the vertebral body in one of a first relative position to create a first lesion adjacent the first active tip and a second lesion adjacent the second active tip, a second relative position to create a symbiotic lesion adjacent the first active tip and the second active tip via positive cooperation therebetween, and a third relative position to create a negative co-operation lesion adjacent the first active tip and the second active tip via negative cooperation therebetween;
   wherein a first plane parallel to a cranial-caudal axis of the patient extends along the first mid-longitudinal axis of the first bipolar probe, a second plane parallel to the cranial-caudal axis of the patient extends along the second mid-longitudinal axis of the second bipolar probe, and, after positioning of the first active tip and the second active tip, the first plane and the second plane intersect one another within the vertebral body; and
   wherein a first coronal plane extends through each of the first bipolar probe and the second bipolar probe, and the first bipolar probe and the second bipolar probe, after positioning of the first active tip and the second active tip within the vertebral body, overlap one another in directions aligned with the cranial-caudal axis in the first coronal plane.

2. The method of claim 1, wherein the symbiotic lesion would have a size greater than the first lesion and the second lesion combined.

3. The method of claim 1, wherein the negative co-operation lesion would have a size smaller than the first lesion and the second lesion combined.

4. The method of claim 1, further comprising positioning the first cannula through a first pedicle, and positioning the second cannula through a second pedicle.

5. The method of claim 1, further comprising:
   determining an ablation zone to be targeted within the vertebral body.

6. The method of claim 5, further comprising:
   determining sizes of the first lesion, the second lesion, the symbiotic lesion, and/or the negative co-operation lesion that would cover the ablation zone.

7. The method of claim 1, further comprising:
cooling, internally, the first bipolar probe and the second bipolar probe during the creation of the first lesion, the second lesion, the symbiotic lesion, and/or the negative co-operation lesion.

8. The method of claim 1, wherein the positioning the first active tip and the positioning the second active tip creates a first acute angle between the first plane and a sagittal plane of the patient, and a second acute angle between the second plane and the sagittal plane of the patient.

9. The method of claim 1, further comprising:
measuring a temperature of an area surrounding the first active tip of the first bipolar probe;
measuring a temperature of an area surrounding the second active tip of the second bipolar probe;
adjusting a power supply to the first bipolar probe based on the measured temperature of the area surrounding the first active tip of the first bipolar probe; and
adjusting a power supply to the second bipolar probe based on the measured temperature of the area surrounding the second active tip of the second bipolar probe.

10. A method of lesioning a region of a vertebral body of a patient, the method comprising:
inserting a first bipolar probe through a first cannula positioned in a first target location in the vertebral body along a first trajectory, the first bipolar probe having a proximal end, an opposite distal end, and a first mid-longitudinal axis extending through the proximal end and the distal end thereof, the first bipolar probe including a first active tip including at least two electrodes;
inserting a second bipolar probe through a second cannula positioned in a second target location in the vertebral body along a second trajectory, the second bipolar probe having a proximal end, an opposite distal end, and a second mid-longitudinal axis extending through the proximal end and the distal end thereof, the second bipolar probe including a second active tip including at least two electrodes;
determining an ablation zone to be targeted within the vertebral body;
measuring a temperature of an area surrounding the first active tip of the first bipolar probe;
measuring a temperature of an area surrounding the second active tip of the second bipolar probe;
supplying power to the first bipolar probe;
supplying power to the second bipolar probe independently from the supplying the power to the first bipolar probe, and
adjusting a power supply to the first bipolar probe based on the measured temperature of the area surrounding the first active tip of the first bipolar probe;
adjusting a power supply to the second bipolar probe based on the measured temperature of the area surrounding the second active tip of the second bipolar probe; and
selectively positioning the first active tip of the first bipolar probe and the second active tip of the second bipolar probe relative to one another in the vertebral body in one of a first relative position to create a first lesion adjacent the first active tip and a second lesion adjacent the second active tip, a second relative position to create a symbiotic lesion adjacent the first active tip and the second active tip via positive cooperation therebetween, and a third relative position to create a negative co-operation lesion adjacent the first active tip and the second active tip via negative cooperation therebetween;
wherein the symbiotic lesion would have a size greater than the first lesion and the second lesion combined, and the negative co-operation lesion would have a size smaller than the first lesion and the second lesion combined;
wherein a first pane parallel to a cranial-caudal axis of the patent extends along the first mid-longitudinal axis of the first bipolar probe, a second plane parallel to the cranial-caudal axis of the patient extends along the second mid-longitudinal axis of the second bipolar probe, and, after positioning of the first active tip and the second active tip, the first plane and the second plane intersect one another within the vertebral body; and
wherein a first coronal plane extends through each of the first bipolar probe and the second bipolar probe, and the first bipolar probe and the second bipolar probe, after positioning of the first active tip and the second active tip within the vertebral body, overlap one another in directions aligned with the cranial-caudal axis in the first coronal plane.

11. The method of claim 10, further comprising positioning the first cannula through a first pedicle, and positioning the second cannula through a second pedicle.

12. The method of claim 10, further comprising:
determining, prior to creation thereof, sizes of the first lesion, the second lesion, the symbiotic lesion, and/or the negative co-operation lesion that would cover the ablation zone.

13. The method of claim 10, further comprising:
cooling, internally, the first bipolar probe and the second bipolar probe during the creation of the first lesion, the second lesion, the symbiotic lesion, and/or the negative co-operation lesion.

14. The method of claim 10, the positioning the first active tip and the positioning the second active tip creating a first acute angle between the first plane and a sagittal plane of the patient, and a second acute angle between the second plane and the sagittal plane of the patient.

15. A method of lesioning a region of a vertebral body of a patient, the method comprising:
positioning a first active tip of a first bipolar probe within the vertebral body;
positioning a second active tip of a second bipolar probe within the vertebral body;
determining an ablation zone to be targeted within the vertebral body;
measuring a temperature of an area surrounding the first active tip of the first bipolar probe;
measuring a temperature of an area surrounding the second active tip of the second bipolar probe;
supplying power to the first bipolar probe in accordance with the measured temperature of the area surrounding the first active tip;
supplying power to the second bipolar probe independently from the supplying the power to the first bipolar probe in accordance with the measured temperature of the area surrounding the second active tip, and
selectively positioning the first active tip of the first bipolar probe and the second active tip of the second bipolar probe relative to one another in the vertebral body in one of a first relative position to create a first lesion adjacent the first active tip and a second lesion adjacent the second active tip, a second relative position to create a symbiotic lesion adjacent the first active tip and the second active tip via positive cooperation therebetween, and a third relative position to create a negative co-operation lesion adjacent the first active tip and the second active tip via negative cooperation therebetween;

wherein the symbiotic lesion would have a size greater than the first lesion and the second lesion combined, and the negative co-operation lesion would have a size smaller than the first lesion and the second lesion combined; and wherein a first plane parallel to a cranial-caudal axis of the patient extends along the first mid-longitudinal axis of the first bipolar probe, a second plane parallel to the cranial-caudal axis of the patient extends along the second mid-longitudinal axis of the second bipolar probe, and, after positioning of the first active tip and the second active tip, the first plane and the second plane intersect one another within the vertebral body, and wherein a first coronal plane extends through each of the first bipolar probe and the second bipolar probe, and the first bipolar probe and the second bipolar probe, after positioning of the first active tip and the second active within the vertebral body, overlap one another in directions aligned with the cranial-caudal axis in the first coronal plane.

* * * * *